United States Patent
Niehaus et al.

(10) Patent No.: US 11,179,049 B2
(45) Date of Patent: Nov. 23, 2021

(54) INTELLIGENT INFLATABLE CUFF FOR ARM-BASED BLOOD PRESSURE MEASUREMENT

(71) Applicant: Fitbit, Inc., San Francisco, CA (US)

(72) Inventors: Logan Niehaus, Alameda, CA (US); Andrew Larsen Axley, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 497 days.

(21) Appl. No.: 15/442,559

(22) Filed: Feb. 24, 2017

(65) Prior Publication Data
US 2017/0245769 A1  Aug. 31, 2017

Related U.S. Application Data

(60) Provisional application No. 62/301,508, filed on Feb. 29, 2016.

(51) Int. Cl.
*A61B 5/022* (2006.01)
*A61B 5/00* (2006.01)
(Continued)

(52) U.S. Cl.
CPC ........ *A61B 5/02225* (2013.01); *A61B 5/0004* (2013.01); *A61B 5/02141* (2013.01);
(Continued)

(58) Field of Classification Search
CPC . A61B 5/02225; A61B 5/022; A61B 5/02216; A61B 5/0002; A61B 5/0004;
(Continued)

(56) References Cited

U.S. PATENT DOCUMENTS 6,331,162 B1   12/2001  Mitchell
6,583,369 B2   6/2003   Montagnino et al.
(Continued)

FOREIGN PATENT DOCUMENTS

EP   1 721 237   8/2012

OTHER PUBLICATIONS

Fuke et al. (Jul. 2013) "Blood pressure estimation from pulse wave velocity measured on the chest," *35th Annual International Conference of the IEEE EMBS*, Osaka, Japan, Jul. 2-3, 2013, 6107-6110.

(Continued)

*Primary Examiner* — Matthew Kremer
*Assistant Examiner* — Avery M Foley
(74) *Attorney, Agent, or Firm* — Dority & Manning, P.A.

(57) ABSTRACT

This disclosure provides devices and methods for estimating blood pressure using intelligent oscillometric blood pressure measurement techniques, where some implementations of the devices include multiple biometric sensors and/or can obtain sensor data from a connected device. In some implementations, the devices automatically determine an identity of a user. In some implementations, the devices automatically provide instructions to users to take blood pressure measurements. In some implementations, the devices applied intelligent inflation techniques to improve user comfort and speed up measurements.

16 Claims, 13 Drawing Sheets

(51) Int. Cl.
*A61B 5/021* (2006.01)
*A61B 5/117* (2016.01)
*A61B 5/1172* (2016.01)
*G16H 40/63* (2018.01)

(52) U.S. Cl.
CPC .............. *A61B 5/117* (2013.01); *A61B 5/1172* (2013.01); *A61B 5/681* (2013.01); *G16H 40/63* (2018.01); *A61B 2560/029* (2013.01)

(58) Field of Classification Search
CPC ............ A61B 5/02141; A61B 5/02152; A61B 5/02158; A61B 5/117; A61B 5/1172; A61B 5/1171; A61B 5/681; A61B 2560/029; G16H 40/60; G16H 40/63; G16H 40/67; G16H 50/00
See application file for complete search history.

(56) References Cited

U.S. PATENT DOCUMENTS

| | | | |
|---|---|---|---|
| 7,479,111 B2 | 1/2009 | Zhang et al. | |
| 8,313,439 B2 | 11/2012 | McCombie et al. | |
| 2005/0143665 A1 | 6/2005 | Huiku et al. | |
| 2008/0043128 A1 | 2/2008 | Poonnen et al. | |
| 2010/0318578 A1* | 12/2010 | Treu | G16H 40/67 707/802 |
| 2010/0331145 A1 | 12/2010 | Lakovic et al. | |
| 2011/0032105 A1 | 2/2011 | Hoffman et al. | |
| 2012/0136605 A1 | 5/2012 | Addison et al. | |
| 2012/0274508 A1 | 11/2012 | Brown et al. | |
| 2013/0106684 A1 | 5/2013 | Weast et al. | |
| 2013/0310700 A1 | 11/2013 | Wiard et al. | |
| 2014/0012117 A1* | 1/2014 | Mensinger | A61B 5/742 600/365 |
| 2014/0099614 A1 | 4/2014 | Hu et al. | |
| 2014/0142403 A1 | 5/2014 | Brumback et al. | |
| 2014/0275854 A1 | 9/2014 | Venkatraman et al. | |
| 2014/0288435 A1 | 9/2014 | Richards et al. | |
| 2014/0358012 A1 | 12/2014 | Richards et al. | |
| 2015/0032009 A1 | 1/2015 | LeBoeuf et al. | |
| 2015/0051500 A1* | 2/2015 | Elliott | A61B 5/6898 600/480 |
| 2015/0112606 A1 | 4/2015 | He et al. | |
| 2015/0366469 A1 | 12/2015 | Harris et al. | |
| 2015/0374249 A1 | 12/2015 | Elliott et al. | |
| 2016/0058375 A1 | 3/2016 | Rothkopf | |
| 2016/0213331 A1 | 7/2016 | Gil et al. | |
| 2016/0261974 A1* | 9/2016 | Arrizza | A61M 1/1603 |
| 2017/0024555 A1* | 1/2017 | Flitsch | G06F 21/32 |
| 2017/0209053 A1 | 7/2017 | Pantelopoulos et al. | |
| 2017/0209055 A1 | 7/2017 | Pantelopoulos et al. | |
| 2017/0251935 A1 | 9/2017 | Yuen et al. | |
| 2017/0281024 A1 | 10/2017 | Narasimhan et al. | |
| 2017/0347895 A1* | 12/2017 | Wei | A61B 5/01 |
| 2018/0078156 A1* | 3/2018 | Chen | A61B 5/117 |

OTHER PUBLICATIONS

Nelson et al. (May 2010) "Noninvasive Measurement of Central Vascular Pressures With Arterial Tonometry: Clinical Revival of the Pulse Pressure Waveform?" *Mayo Clin Proc.*, 85(5):460-472.
Payne et al., (Jan. 2006) "Pulse transit time measured from the ECG: an unreliable marker of beat-to-beat blood pressure," *J Appl Physiol*, 100:136-141.
U.S. Appl. No. 15/406,501, filed Jan. 13, 2017, Pantelopoulos et al.
U.S. Appl. No. 15/414,425, filed Jan. 24, 2017, Pantelopoulos et al.
U.S. Appl. No. 15/452,047, filed Mar. 7, 2017, Yuen.
U.S. Office Action dated Sep. 27, 2019, in U.S. Appl. No. 15/406,501.
U.S. Office Action dated Oct. 1, 2019, in U.S. Appl. No. 15/452,047.
U.S. Final Office Action dated Mar. 11, 2020, in U.S. Appl. No. 15/406,501.
U.S. Office Action dated Apr. 6, 2020, in U.S. Appl. No. 15/414,425.
U.S. Final Office Action dated May 5, 2020, in U.S. Appl. No. 15/452,047.
U.S. Office Action dated May 20, 2020, in U.S. Appl. No. 15/406,501.
U.S. Final Office Action dated Oct. 9, 2020, in U.S. Appl. No. 15/406,501.
U.S. Notice of Allowance dated Dec. 9, 2020, in U.S. Appl. No. 15/406,501.
U.S. Final Office Action dated Jul. 21, 2020, in U.S. Appl. No. 15/414,425.
U.S. Office Action dated Feb. 3, 2021, in U.S. Appl. No. 15/452,047.

\* cited by examiner

INTELLIGENT INFLATABLE CUFF FOR ARM-BASED BLOOD PRESSURE MEASUREMENT

CROSS REFERENCE TO RELATED APPLICATIONS

This application claims benefits under 35 U.S.C. § 119(e) to U.S. Provisional Patent Application No. 62/301,508, entitled: Intelligent Inflatable Cuff for Arm-based Blood Pressure Measurement, filed Feb. 29, 2016, which is herein incorporated by reference in its entirety for all purposes.

INTRODUCTION

This disclosure provides devices and methods for intelligently estimating blood pressure, where some implementations of the devices include multiple biometric sensors and/or can obtain sensor data from a connected device.

Blood pressure is an important health indicator measured in both clinical and nonclinical settings. Many automated systems for measuring a user's blood pressure may use an oscillometric blood pressure measurement (OBPM) technique. An OBPM technique may involve a cuff with an inflatable air bladder that is wrapped around the arm and pumped with air to exert pressure on the arm.

OBPM systems are widely used, primarily because they are easier to use than other alternative methods and do not require a trained operator as compared to the traditional auscultatory method. However, existing OBPM systems can have various limitations. For instance, some OBPM systems are not as accurate as some other types of BP measurement, such as auscultatory methods or tonometry. This inaccuracy is thought to arise from a number of factors inherent to mechanism of the technique, such as sensitivity to motion artifacts, and variability caused by arm posture and cuff placement.

The pressure signal captured by OBPM is affected by hydrostatic pressure, which is affected by cuff placement relative to the heart. Some existing OBPM systems require placement of the measuring device around the upper arm at the heart level to cause the hydrostatic pressure to be nearly equivalent to the hydrostatic pressure at the heart. Other existing OBPM systems can be placed around the wrist, but such systems require particular arm posture and position to factor out the effect of hydrostatic pressure, which is not always properly executed in practice.

SUMMARY

This disclosure provides devices and methods for intelligently estimating blood pressure oscillometric blood pressure measurement techniques, where some implementations of the devices include multiple biometric sensors and/or can obtain sensor data from a connected device.

One aspect of the disclosure relates to methods of obtaining blood pressure data, implemented using an intelligent oscillometric blood pressure measurement (IOBPM) device. The IOBPM device includes an inflatable cuff, a pressure sensor, communication circuitry, a memory, and one or more processors. The method involves: obtaining, by the one or more processors, data associated with a user; determining, by the one or more processors, an identity of the user based on the data associated with the user; obtaining, by the one or more processors, blood pressure data from the user, wherein the blood pressure data are generated by the pressure sensor; and sending, through the communication circuitry, data indicating the identity of the user and the blood pressure data to a second device. In some implementations, the method further involves storing the blood pressure data in a user account associated with the identity of the user.

In some implementations, the pressure sensor is selected from: a force sensor, a force sensitive resistor, a mechanical sensor, a load sensor, a load cell, a strain gauge, a piezo sensor, a membrane potentiometer, etc.

In some implementations, the communication circuitry employs a wired or wireless communication protocol.

In some implementations, the second device is associated with the user, and the data associated with the user and obtained by the one or more processors include data indicative of the intelligent oscillometric blood pressure measurement device being paired with the second device through a wireless communication protocol. In some implementations, the second device is associated with the user via a hardware characteristic of the mobile device or via credentials received from an application running on the mobile device. In some implementations, the second device is the closest connectable device.

In some implementations, the data associated with the user include biometric data, and wherein determining the identity of the user includes providing the biometric data to a classifier to determine the identity of the user. In some implementations, the biometric data are selected from: motion data, ECG data, PPG data, blood pressure data, arm circumference data, bioelectrical impedance analysis (BIA) data, finger print sensor data, etc. In some implementations, the data associated with the user include user input specifying the identity of the user. In some implementations, the data associated with the user include data generated by one or more sensors of the intelligent oscillometric blood pressure measurement device. In some implementations, the data obtained by the one or more processors include data that are generated on the second device and obtained through the communication circuitry.

In some implementations, the intelligent oscillometric blood pressure measurement device includes a user interface, wherein the method further including displaying the identity of the user or information derived therefrom on the user interface of the intelligent oscillometric blood pressure measurement device.

In some implementations, the second device includes a user interface, wherein the method further including displaying the identity of the user or information derived therefrom on the user interface of the second device.

Another aspect of the disclosure relates to methods of obtaining blood pressure data, implemented using an intelligent oscillometric blood pressure measurement device and a second device. The intelligent oscillometric blood pressure measurement device includes an inflatable cuff, a pressure sensor, and first communication circuitry. The second device includes a memory, second communication circuitry, and one or more processors. The method involves: receiving, by the second device, blood pressure data from the intelligent oscillometric blood pressure measurement device via the first communication circuitry and the second communication circuitry. The blood pressure data are obtained from a user and generated by the pressure sensor of the intelligent oscillometric blood pressure measurement device. The method further involves determining an identity of the user using the blood pressure data, other biometric data associated with the user, or non-biometric data associated with the user. In some implementations, determining the identity of the user associated with the blood pressure data involves providing the blood pressure data to a classifier to determine the identity of the user.

In some implementations, the method further includes causing the blood pressure data to be stored in an account associated with the identity of the user.

In some implementations, determining the identity of the user associated with the blood pressure data includes: providing the blood pressure data to a classifier to determine the identity of the user. In some implementations, determining the identity of the user associated with the blood pressure data includes: obtaining from the user the other biometric data; and providing the other biometric data to a classifier to determine the identity of the user.

In some implementations, the second device includes one or more biometric sensors, and wherein the other biometric data include data generated by the one or more biometric sensors of the second device.

In some implementations, the intelligent oscillometric blood pressure measurement device includes one or more additional biometric sensors in addition to the pressure sensor, and wherein the other biometric data include data generated by the one or more additional biometric sensors of the intelligent oscillometric blood pressure measurement device and the other biometric data are obtained through communication between the first communication circuitry and the second communication circuitry.

In some implementations, the other biometric data are selected from: motion data, ECG data, PPG data, blood pressure data, arm circumference data, BIA data, finger print sensor data, etc.

In some implementations, the non-biometric data associated with the user include data indicating that the second device is associated with the user. In some implementations, the second device is associated with the user via a hardware characteristic of the second device or via credentials received from an application running on the second device. In some implementations, the second device is associated with the user via a hardware characteristic of the second device or via credentials received from an application running on the second device.

A further aspect of the disclosure relates to methods of obtaining blood pressure data, implemented using an oscillometric blood pressure device. The oscillometric blood pressure device includes an inflatable cuff, a pressure sensor, communication circuitry, and one or more processors communicatively linked to the pressure sensor and the communication circuitry. The method involves: receiving, by using the communication circuitry, data of a user from a second device; determining, by the one or more processors, that conditions for measuring a blood pressure are satisfied based on the data of the user; instructing the user to take a blood pressure measurement; and obtaining, by the one or more processors, blood pressure data provided by the pressure sensor. In some implementations, the oscillometric blood pressure device includes a user interface. Instructing the user involves: displaying a visual instruction or visual cue through the user interface, playing an auditory instruction or auditory cue through the user interface, vibrating the oscillometric blood pressure device, etc.

In some implementations, instructing the user includes: sending, by using the communication circuitry, the instruction to the second device, and providing the instruction by using the second device. In some implementations, providing the instruction by using the second device includes an operation selected from: displaying a visual instruction or visual cue by using the second device, playing an auditory instruction or auditory cue by using the second device, vibrating the second device, etc.

In some implementations, the data of the user includes biometric data. In some implementations, the second device includes one or more biometric sensors configured to collect the biometric data. In some implementations, the biometric data are selected from: sleeping, waking, heart rate or heartbeat waveform, amount and composition of food consume, motion, activity, etc.

In some implementations, the second device includes a wearable device worn by the user. In some implementations, the wearable device is configured as a wrist worn device. In some implementations, the second device includes a smart phone.

In some implementations, the conditions for measuring a blood pressure are selected from: having no recent exercises or steps, having no erratic motions, physiological stress, or elevated heart rate, having low heart rate variability, not having recently consumed food or drugs, having recently ended a commute, having recently waken up, approaching the usual sleeping time of the user, etc.

In some implementations, the conditions for measuring a blood pressure are selected from: having recent exercises or steps, having physiological stress or elevated heart rate, having high heart rate variability, having recently consumed food or drugs, etc.

Another aspect relates to methods of measuring blood pressure using a blood pressure device, which includes an inflatable cuff, a pressure sensor, a pump, and one or more processors communicatively linked to the pressure sensor and the pump. The method includes: determining, by the one or more processors, a target inflation pressure based on data characterizing a user; inflating, using the pump, the inflatable cuff to the target inflation pressure; and obtaining, by the one or more processors, blood pressure data provided by the pressure sensor. In some implementations, determining the target inflation pressure based on the data characterizing the user involves: determining, by the one or more processors, an identity of the user based on the data characterizing the user; accessing, by the one or more processors, one or more stored blood pressure values linked to the identity of the user; and determining, by the one or more processors, the target inflation pressure relative to the one or more stored blood pressure values.

In some implementations, determining the identity of the user based on the data characterizing the user includes providing the data to a classifier to determine the identity of the user.

In some implementations, the blood pressure device further includes communication circuitry, and wherein accessing the one or more stored blood pressure values includes: obtaining, through the communication circuitry, the one or more stored blood pressure values from a second device.

In some implementations, the one or more stored blood pressure values includes one or more previously recorded systolic blood pressures associated with the user.

In some implementations, the blood pressure device includes an intelligent oscillometric blood pressure measurement device.

In some implementations, the data characterizing the user include biometric data. In some implementations, the blood pressure device includes one or more biometric sensors configured to collect the biometric data.

In some implementations, the data characterizing the user include demographic data of the user. In some implementations, the demographic data of the user are selected from age, gender, height, weight and information related thereof, etc.

In some implementations, determining the target inflation pressure includes: calculating, by the one or more processors, when inflating the cuff, estimates of systolic and/or diastolic pressure of the user, and calculating, by the one or more processors, a target pressure using the estimates of systolic and/or diastolic pressure.

In some implementations, determining the target inflation pressure includes: using a PPG sensor placed distal to the center of the inflatable pressure cuff to detect a cessation or near cessation of the pulse; and determining the target inflation pressure relative to a pressure of the inflatable cuff when the cessation or near cessation of the pulse is detected.

In some implementations, inflating the inflatable cuff to the target inflation pressure includes: inflating the inflatable cuff to a first pressure at a first one or more speeds, and inflating the inflatable cuff from the first pressure to a second pressure at a second one or more speeds.

In some implementations, the first pressure is lower than the second pressure, and the first one or more speeds are higher on average than the second one or more speeds. In some implementations, the first pressure is below an estimate of a diastolic pressure and the second pressure is above an estimate of a systolic pressure.

In some implementations, the method further includes determining the identity of the user, and wherein the estimate of the diastolic pressure and the estimate of the systolic pressure are based at least in part on data associated with the identity of the user.

In some implementations, the method further includes obtaining biometric data collected from the user, and determining the identity of the user based on biometric data collected from the user.

In some implementations, the method further includes, before the inflatable cuff is inflated to the target inflation pressure: inflating a pre-inflation bladder to a pre-inflation pressure higher than atmospheric pressure; and releasing air from the pre-inflation bladder to the inflatable cuff.

In some implementations, the pre-inflation pressure is based at least in part on the target inflation pressure or an expected diastolic pressure.

In some implementations, the method further includes, after the inflatable cuff is inflated to the target inflation pressure, controlling the release of air from the inflatable cuff, wherein obtaining blood pressure data provided by the pressure sensor includes obtaining blood pressure data before and after the inflatable cuff is inflated to the target inflation pressure.

In some implementations, the method further includes, calculating a composite blood pressure value using the blood pressure data obtained before and the blood pressure data obtained after the inflatable cuff is inflated to the target inflation pressure. In some implementations, the blood pressure is calculated as a weighted average of the blood pressure data obtained before and the blood pressure data obtained after the inflatable cuff is inflated to the target inflation pressure.

A further aspect of the disclosure relates to methods of measuring blood pressure, implemented using a oscillometric blood pressure device including an inflatable cuff, a pressure sensor, at least one other biometric sensor, and one or more processors communicatively linked to the pressure sensor and the at least one other biometric sensor. The method involves: inflating the inflatable cuff to an inflation pressure; obtaining, by the one or more processors, pressure data provided by the pressure sensor; obtaining, by the one or more processors, other biometric data provided by the at least one other biometric sensor; and estimating a blood pressure value using the pressure data and the other biometric data. In some implementations, the at least one other biometric sensor includes one or more of the following: inertial sensors, acoustic sensors, electrocardiogram (ECG) sensors, photoplethysmograph (PPG) sensors.

In some implementations, the other biometric data include motion data and wherein estimating a blood pressure value includes using the motion data to reject motion artifacts from the pressure data. In some implementations, using the motion data to reject motion artifacts from the pressure data includes: identifying a motion component from the motion data, identifying a pressure component corresponding to the motion component, and removing the pressure component from the pressure data.

In some implementations, the other biometric data include inertial data generated from an inertial sensor at the inflatable cuff, and wherein estimating the blood pressure value includes: obtaining orientation or placement information of the inflatable cuff using the inertial data; selecting parameter values based on the orientation or placement information; and calculating one or more blood pressure values using the pressure data and the selected parameter values.

In some implementations, the method further includes: instructing the user to adjust a placement or an orientation of the inflatable cuff when the obtained orientation or placement information indicates an improper orientation or placement.

In some implementations, the other biometric data include inertial data generated from an inertial sensor, and wherein estimating the blood pressure value includes: determining a posture of the use using the inertial data; selecting parameter values based on the posture; and calculating one or more blood pressure values using the pressure data and the selected parameter values.

Systems and devices are also provided to implement the methods above. An additional aspect of the disclosure relates to intelligent oscillometric blood pressure devices. In some implementations, an intelligent oscillometric blood pressure device includes: an inflatable cuff including at least one pressure sensor; a memory; communication circuitry; and one or more processors communicative linked to the pressure sensor, the memory, and the communication circuitry. The one or more processors are configured to: determine an identity of a user based on data obtained by the one or more processors; obtain blood pressure data of the user using the pressure sensor; and operate the communication circuitry to send data indicating the identity of the user and the blood pressure data to a second device. In some implementations, the device also includes one or more the following biometric sensors: inertial sensors, acoustic sensors, electrocardiogram (ECG) sensors, photoplethysmograph (PPG) sensors, etc. In some implementations, the ECG sensors include an electrode mounted on the inside of the cuff and an electrode mounted on the outside of the cuff. In some implementations, the device further includes a user interface communicatively linked to the one or more processors.

These and other objects and features of the present disclosure will become more fully apparent from the following description, with reference to the associated drawings and appended claims.

DETAILED DESCRIPTION

Introduction

Figure 1:
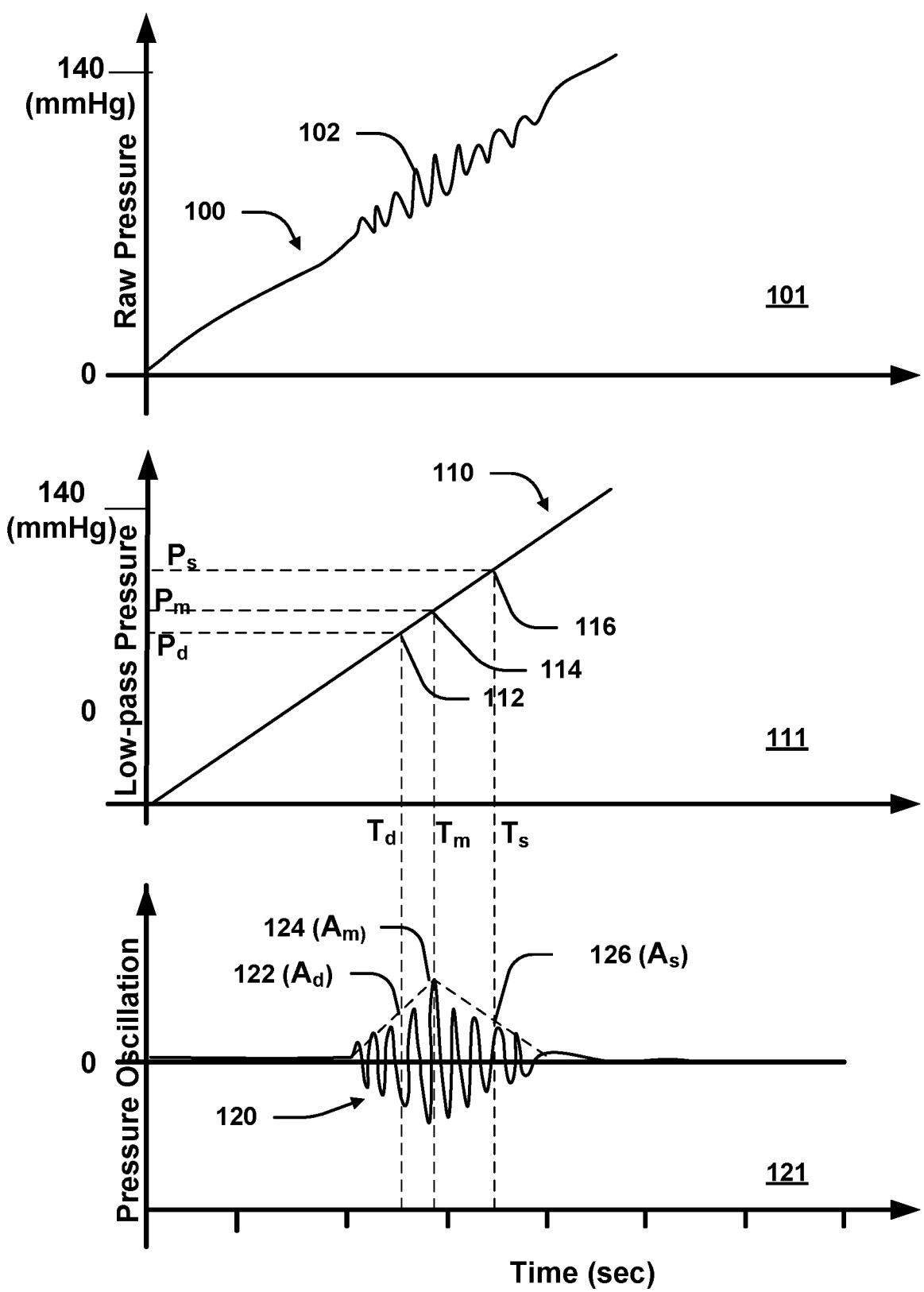
FIG. 1 shows a diagram illustrating how an OBPM device can use a relationship between pressure oscillation and blood pressure to provide estimates of blood pressure.

Unless otherwise specified, the word "or" as used herein describes a non-exclusive relation, such that "A or B" means A, B, or A and B, instead of either A or B, but not A and B. In other words, the word "or" is synonymous to "and/or" unless otherwise specified.

Various embodiments of the disclosure improve one or more aspects of conventional OBPM devices. For example, in some implementations, an intelligent OBPM (IOBPM) device can provide a connected experience by connecting with a second device (e.g., a mobile phone, a wearable activity tracker, a scale, or any other suitable computer device). In such a connected experience, the IOBPM device, the second device, or a combination of the two can automatically determine the identity of the user from whom blood pressure data are obtained. The IOBPM system can leverage the user identity to enable the blood pressure measurement device to customize or identify an inflation profile of an inflatable cuff for the user.

Various conventional OBPM technologies require pressures capable of nearly occluding the artery, causing discomfort to the user. Some conventional OBPM technologies require slowly increasing and/or decreasing pressure applied to occlude the artery. A measurement cycle may take 30 seconds to 1 minute to complete, sustaining a relatively long period of discomfort to the user. If the pressure change is applied at a higher speed, measurement accuracy may be compromised. Some implementations of the disclosure provide IOBPM systems that can automatically determine the identity of the user and leverage the user identity to enable the blood pressure measurement device to customize or identify an inflation profile of an inflatable cuff for the user. Customizing and/or identifying an inflation profile of an inflatable cuff for the user can, in some cases, result in improvements to the speed in which cuff inflation can occur without compromising accuracy in a significant way. Additionally or alternatively, such inflation profiles can assist an IOBPM device to avoid unnecessarily high cuff pressure. These advantages, individually or in combination, can improve user comfort and measurement speed.

Various existing OBPM systems do not customize the device for different users, or do not provide efficient ways to organize data of multiple users. Some implementations of the disclosure provide IOBPM systems that can use the detected identity of the user to automatically manage biometric data obtained from the IOBPM systems. For example, upon identifying the identity of the user, the IOBPM device can automatically communicate the blood pressure data to a server in a manner which causes the server to log the blood pressure with the user account linked to the user identity.

Blood pressure measurements can be influenced by various contextual factors existing at or near the time when blood pressure measurements are taken. Such contextual factors include food intake, caffeine consumption, body posture, physical activities, etc. These contextual factors cause variation in blood pressure that is undesirable or confounding. Conventional OBPM technologies do not effectively address these undesirable or confounding contextual factors. In some implementations of the disclosure, the IOBPM device can obtain data associated with the user from the second device and analyze the data to determine conditions for measuring blood pressure are satisfied. Based on the satisfaction of the conditions, the IOBPM system can provide instructions to the user to take a blood pressure measurement. In some cases, the conditions are set based on contextual factors that can influence blood pressure measurements, such as food intake, caffeine consumption, and physical activities. The instructions help to control or factor out these contextual factors, which allows for improved data collection and/or data analysis of blood pressure data. By way of example and not limitation, some implementations provide a device that can automatically detect that a user has recently engaged in a physical activity that may cause blood pressure to temporally fluctuate, and automatically instructs the user to delay taking a blood pressure measurement until the effect of the activity subsides.

In some implementations, an IOBPM device has the ability to obtain other biometric data (e.g., from biometric sensors of the IOBPM device or from the second device) in addition to blood pressure data and use the other biometric data to remove motion artifact or control for other factors (e.g., sensor placement, posture, and device orientation) that affect blood pressure measurements. This helps to improve accuracy of blood pressure estimates. In some implementations, this allows flexible placement or adjusted placement of the IOBPM device without being constrained to a posture where the OPBM is aligned with the user's heart.

Example embodiments discussed in the foregoing involve an IOBPM device configured to measure the blood pressure of a user. As such, one example technique that an IOBPM device may implement is now described in greater detail. To begin, it is to be appreciated that when an external pressure in a certain pressure range is applied to the tissue exterior to an arterial blood vessel, the oscillation of the blood vessel induces a measurable pressure oscillation at the tissue exterior to the arterial blood vessel. Accordingly, the IOBPM device may apply varying external pressures to the tissue of a user (e.g., via an inflatable cuff) and then detect and/or characterize pressure oscillations of the blood while the varying external pressure is applied. The IOBPM device may then use a relationship between pressure oscillation and blood pressure to derive the user's blood pressure from the detected and/or characterized oscillations.

FIG. 1 is a diagram illustrating how an IOBPM device can use a relationship between pressure oscillation and blood pressure to provide estimates of blood pressure. The top panel 101 of FIG. 1 shows schematic external pressure data 100 that can be observed as increasing external pressure is applied to the external tissue of an artery (e.g., by a pressure cuff around an arm or a wrist). Shown on the horizontal axis is time measured in seconds and on the vertical axis is pressure measured in mmHg. As the external pressure increases and becomes closer to the diastolic and systolic blood pressures, the IOBPM device detects that the artery starts to oscillate and oscillation pressure can be observed as shown at portion 102. It is to be appreciated that the illustration of the oscillation shown in FIG. 1 is exaggerated and simplified to clarify the concepts discussed herein.

The middle panel 111 of FIG. 1 shows the external pressure 110 without the oscillation, which can be obtained, for example, by application of a low-pass filter. The bottom panel 121 of FIG. 1 shows the oscillation pressure only, which can be obtained, for example, by application of a high-pass filter. The oscillation data 120 increases and then decreases in amplitude. The illustration portrays a linear increase and decrease, however these changes may be non-linear. It reaches its maximum amplitude $A_m$ at $T_m$, at point 124, corresponding to point 114 when the external pressure equals the mean arterial pressure $P_m$. As the external pressure increases and approaches $P_m$, the oscillation increases and reaches maximum amplitude at $P_m$. Thereafter, as the external pressure continues to increase, the oscillation amplitude decreases. The amplitude of the oscillation and its relation to the diastolic pressure and the systolic pressure can be empirically determined. For instance, some empirical algorithm identifies the diastolic pressure $P_d$ at point 112 (below $P_m$) corresponding to an amplitude of the oscillation at $A_d$ at point 122 before it reaches $A_m$, such that $A_d/A_m$ equals 0.85. Some empirical algorithm identifies the systolic pressure $P_s$ at point 116 (above $P_m$) as corresponding to an amplitude of the oscillation at $A_s$ at point 126 after it reaches $A_m$, such that $A_s/A_m$=0.55. Other algorithms may be empirically derived to estimate diastolic pressure and systolic pressure. Various implementations of the current disclosure exploit the relation between blood pressure and oscillation signal.

Connected IOBPM Device

Figure 2:
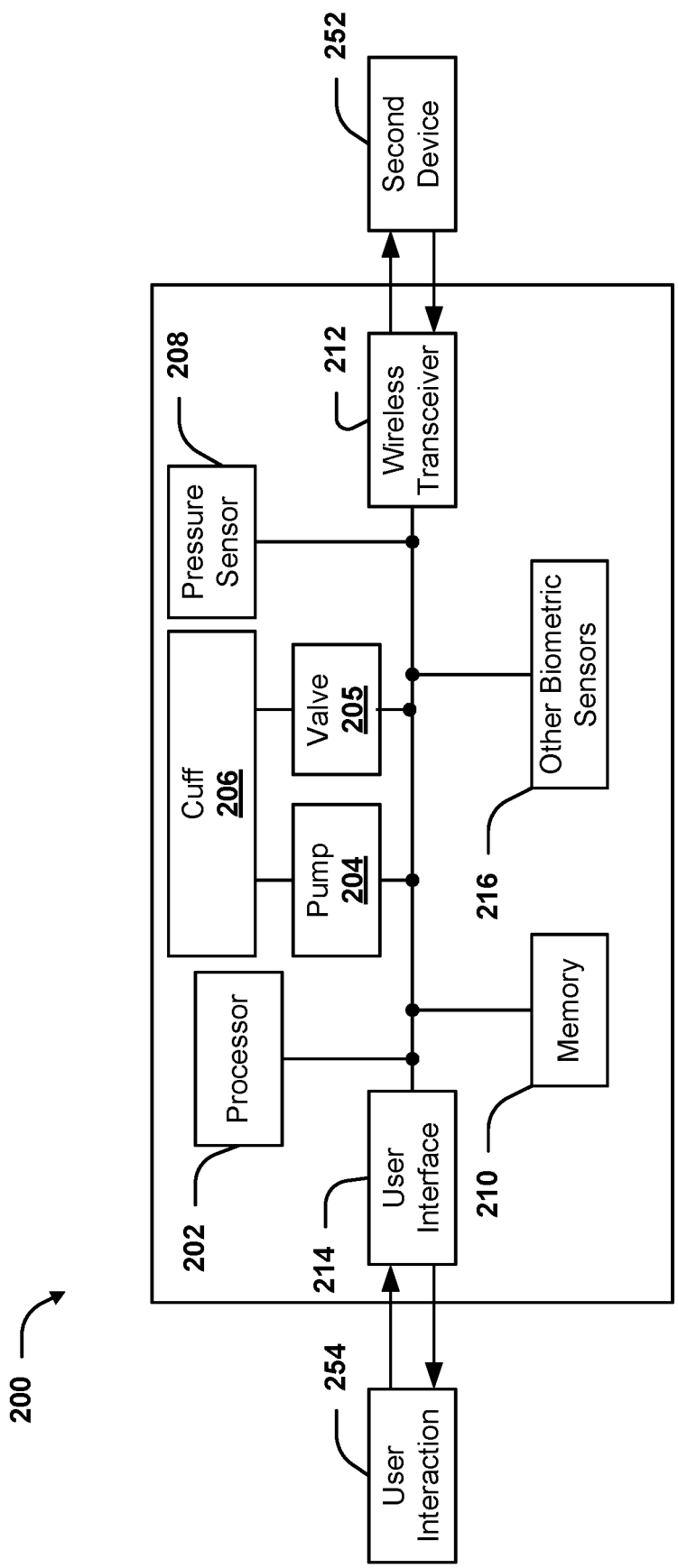
FIG. 2 shows a block diagram of a blood pressure measurement device, according to some implementations of the disclosure.

FIG. 2 shows a block diagram of an intelligent blood pressure measurement device, according to some implementations of the disclosure. The device 200 shown in FIG. 2 includes a processor 202, a pump 204, a valve 205, an inflatable cuff 206, a pressure sensor 208, memory 210, a wireless transceiver 212, and a user interface 214. It is to be appreciated that different embodiments of the device 200 can have more or less components shown in FIG. 2. For example, in some cases, the device 200 may have more than one processors, pumps, valves, inflatable cuffs, pressure sensors, memory, wireless transceivers, and user interfaces. Alternatively or additionally, the device may lack a processor, a pump, a valve, an inflatable cuff, a pressure sensor, memory, a wireless transceiver, and a user interface.

The pump 204 may be connected to the inflatable cuff 206 via the valve 205. The device 200 may increase external pressure applied to the tissue of the user by operating the pump 204 to supply air to a bladder in the inflatable cuff 206 through the valve 205.

As discussed above, the blood pressure measurement device 200 may also include a pressure sensor 208. In some implementations, the pressure sensor 208 is placed in or near the pressure cuff 206. In various implementations, the pressure sensor 208 can include one or more of the following: a force sensor, a force sensitive resistor, a mechanical sensor, a load sensor, a load cell, a strain gauge, a piezo sensor, or a membrane potentiometer.

The wireless transceiver 212 allows the blood pressure measurement device 200 to communicate and exchange data through a wireless connection protocol with a second device 252. Wireless communication protocols and methods may include but are not limited to Wi-Fi, Bluetooth, NFC, Infrared, and ZigBee. In alternative implementations, the blood pressure measurement device may be connected to the second device 252 through a wired connection, such as by a USB connection, a serial connection, a parallel port connection, a lightning connection, or a CAT5 connection.

The processor 202 is communicatively linked to the memory 210, the pump 204, and the valve 205, the pressure sensor 208, and the wireless transceiver 212. The memory 210 stores program instructions that can be executed by the processor 202 to control various elements of the blood pressure measurement device 200. Memory 210 can also store sensor data such as blood pressure data that is obtained from pressure data generated by the pressure sensor or data calculated therefrom. The other data disclosed in this disclosure may also be stored in the memory 210. To clarify the description herein, the phrase "the processor is configured to" may signify, in accordance with some embodiments, operations performed by the processor based on executing the instructions stored in the memory 210.

The processor 202 is configured to control operations of the pump 204 and the valves 205. In some implementations, the processor 202 controls the opening and/or closing of the at least one release valve 205 during the deflation and/or inflation of the inflatable cuff 206. In some implementations, the at least one valve 205 includes at least one variable-speed valve for releasing air from the pressure cuff 206. In some implementations, the at least one valve 205 includes two or more valves with different flow rates for releasing air from the pressure cuff 206.

The processor 102 may also be configured to operate the pressure sensor 208 and/or obtain pressure data from the pressure sensor 208. The processor 202 is configured to control the wireless transceiver 212 to exchange data between the blood pressure measurement device 200 and the second device 252. Blood pressure measurement device 200 optionally includes one or more other biometric sensors 216 in addition to the pressure sensor 208. In some implementations, the other biometric sensors 216 may include one or more inertial sensors, acoustic sensors, electrocardiogram (ECG) sensors, and photoplethysmograph (PPG) sensors. In other implementations, the other biometric sensors 216 may include one or more sensors described hereinafter, including sensors described in association with a secondary device such as a wearable biometric monitoring device.

Blood pressure measurement device 200 optionally includes a user interface 214. The user interface 214 allows provision of output data to the user and reception of input data from the user, as shown in user interaction 254.

User Interface with the IOBPM Device

The blood pressure measurement device may include one or more mechanisms for interacting with the device either locally or remotely. In one embodiment, the blood pressure measurement device may convey data visually through a digital display. The physical embodiment of this display may use any one or a plurality of display technologies including, but not limited to one or more of LED, LCD, AMOLED, E-Ink, Sharp display technology, graphical display, and other display technologies such as TN, HTN, STN, FSTN, TFT, IPS, and OLET. This display could show data acquired or stored locally on the device or could display data acquired remotely from other devices or Internet services. The device may use a sensor (for example, an Ambient Light Sensor, "ALS") to control or adjust screen backlighting. For example, in dark lighting situations, the display may be dimmed to conserve battery life, whereas in bright lighting situations, the display may increase its brightness so that it is more easily read by the user.

In another embodiment, the device may use single or multicolor LEDs to indicate a state of the device. States that the device indicate may include but are not limited to biometric states such as heart rate or application states such as an incoming message, a goal has been reached. These states may be indicated through the LED's color, being on, off, an intermediate intensity, pulsing (and/or rate thereof), and/or a pattern of light intensities from completely off to highest brightness. In one embodiment, an LED may modulate its intensity and/or color with the phase and frequency of the user's heart rate.

In one embodiment, the use of an E-Ink display would allow the display to remain on without the battery drain of a non-reflective display. This "always-on" functionality may provide a pleasant user experience in the case of, for example, a watch application where the user may simply glance at the device to see the time. The E-Ink display always displays content without compromising the battery life of the device, allowing the user to see the time as they would on a traditional watch.

The device may use a light such as an LED to display the heart rate of the user by modulating the amplitude of the light emitted at the frequency of the user's heart rate. The device may depict diastolic pressure, systolic pressure, heart rates, heart rate zones (e.g., aerobic, anaerobic) through the color of an LED (e.g., green, red) or a sequence of LEDs that light up in accordance with changes in blood pressure or heart rate (e.g., a progress bar). The device may be integrated or incorporated into another device or structure, for example, glasses or goggles, or communicate with glasses or goggles to display this information to the user.

The blood pressure measurement device may also convey information to a user through the physical motion of the device. One such embodiment of a method to physically move the device is the use of a vibration inducing motor. The device may use this method alone, or in combination with a plurality of motion inducing technologies.

The device may convey information to a user through audio. A speaker could convey information through the use of audio tones, voice, songs, or other sounds.

These three information communication methods—visual, haptic, and auditory—may be used alone or in any combination with each other or another method of communication to communicate any one or plurality of the following information:

A message or indicator instructing the user to obtain a blood pressure measurement The device has started, ended, or failed a measurement of blood pressure The user's blood pressure has reached a certain level The user has a normal, active, or resting heart rate of a specific value or in a specific range The user's blood pressure or heart rate has enter or exited a certain goal range or training zone The user has a new heart rate "zone" goal to reach, as in the case of heart rate zone training for running, bicycling, swimming, etc.

In some implementations, the blood pressure measurement device includes a user interface for receiving user input through, e.g., a touch screen, one or more buttons, or one or more touch sensitive surface.

User Interface with a Secondary Device

In an embodiment, an IOBPM device may transmit and receive data and/or commands to and/or from a secondary electronic device. The secondary electronic device may be in direct or indirect communication with the IOBPM device. Direct communication refers herein to the transmission of data between a first device and a secondary device without any intermediary devices. For example, two devices may communicate to one another over a wireless connection (e.g., Bluetooth) or a wired connection (e.g., USB). Indirect communication refers to the transmission of data between a first device and a secondary device with the aid of one or multiple intermediary devices which relay the data. Intermediary devices may include but are not limited to a wireless repeater (e.g., Wi-Fi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In one embodiment, the secondary device which acts as a user interface to the blood pressure measurement device may consist of a smartphone, although it is to be understood that any other computer device is consistent with the embodiments contemplated herein, such as a desktop, tablet, gaming system, set-top box, another wearable device, or any other suitable computer device. An app on the smart phone may facilitate and/or enable the smartphone to act as a user interface to the blood pressure measurement device. The blood pressure measurement device may send biometric and other data to the smartphone in real-time or with some delay. The smart phone may send a command or commands to the biometric device for example to instruct it to send biometric and other data in real-time or with some delay.

The smartphone may have one or multiple apps to enable the user to view data from their biometric device or devices. The app may by default open to a "dashboard" page when the user launches or opens the app. On this page, summaries of data totals such as blood pressures, heart rate may be shown. Other pertinent information such as when the last time the app received data from the blood pressure measurement device, metrics regarding the activities, step counts, sleep states, etc., may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping may enable the user to navigate through current and previous metrics.

Device Configuration

Figure 3A:
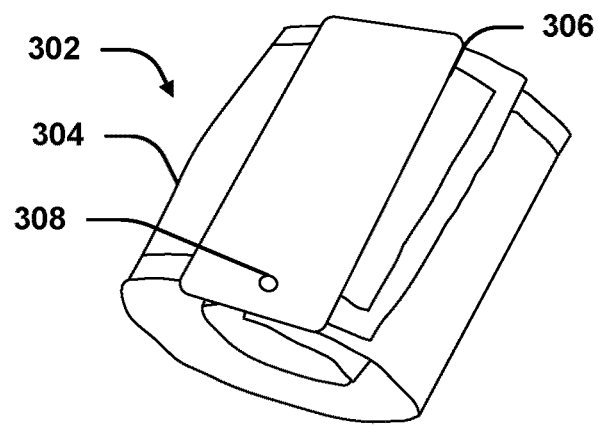
FIG. 3A-3C shows three blood pressure measurement devices in three different implementations.
Figure 3B:
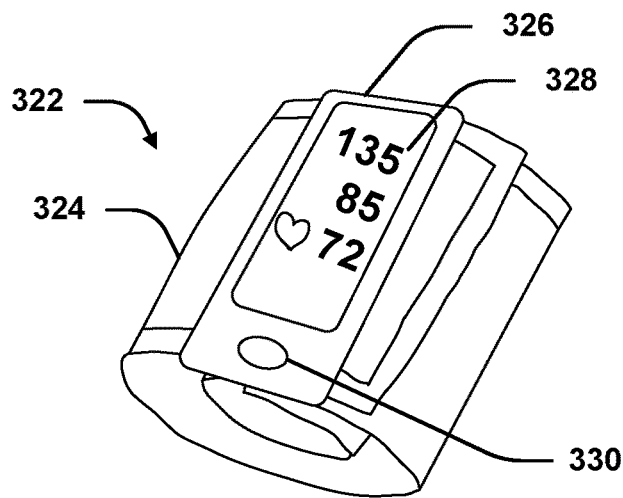
Figure 3C:
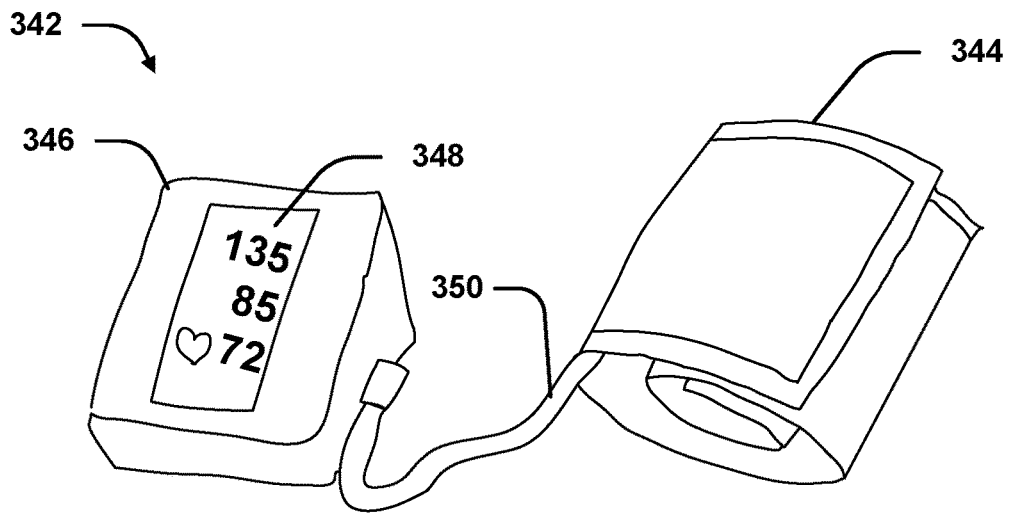

FIGS. 3A-3C shows three IOBPM devices in three different implementations. FIG. 3A illustrates an IOBPM device 302 including an inflatable cuff 304 and a housing 306 attached to the inflatable cuff 304. The housing 304 can enclose one or more elements similar to those described in association with the blood pressure device 200 of FIG. 2, including the processor 202, the pump 204 and the valve 205, the pressure sensor 208, the wireless transceiver 212, the biometric sensors 216, and the memory 210. The blood pressure measurement device 302 also includes an LED indicator 308, which can be configured to display information as a user interface element. In addition, as described above, the device 302 can exchange data with a second device, where the second device has a user interface that can be used to display information obtained from the IOBPM device 302 (e.g., systolic blood pressure, diastolic blood pressure, heart rate, other biometric data, and user identity information) and obtain information that can be sent to the blood pressure measurement device 302.

FIG. 2B illustrates an IOBPM device 322 according to some implementations, which is similar to device 302, but additionally includes a display 328 and an electrode contact 330 exposed on an exterior surface of a housing 326. The device 322 also includes the housing 326 attached to an inflatable cuff 324. The display 328 provides a user interface for displaying data generated or obtained by device 322 (e.g., systolic blood pressure, diastolic blood pressure, heart rate, other biometric data, and user identity information). In some implementations, the display 328 can display user instructions. In some implementations, the display 328 includes a touchscreen that allows device 323 to receive user input from the touchscreen, e.g., user identity information specified by a user. The blood pressure measurement device 322 includes an ECG electrode contact 330 exposed on the housing of 326. Hidden from view is a second ECG electrode disposed on an interior surface of cuff 324 configured to contact the skin of the user when the cuff is worn on the skin. The ECG electrode 330 is configured to allow the user to touch the electrode 330 using a hand or arm not wearing the cuff, thereby creating a closed electrical path to generate ECG data.

FIG. 2C illustrates an IOBPM 342 according to some implementations. Device 342 includes a housing 346 to an inflatable cuff 344 through an air tube 350. Housing 346 encloses elements similar to those enclosed in housing 306, including a pump, which can supply air through the air tube 350 to the inflatable cuff 344. Device 342 also includes a display exposed on a surface of the house 346, with similar features as those of the display 328 described above.

Figure 4:
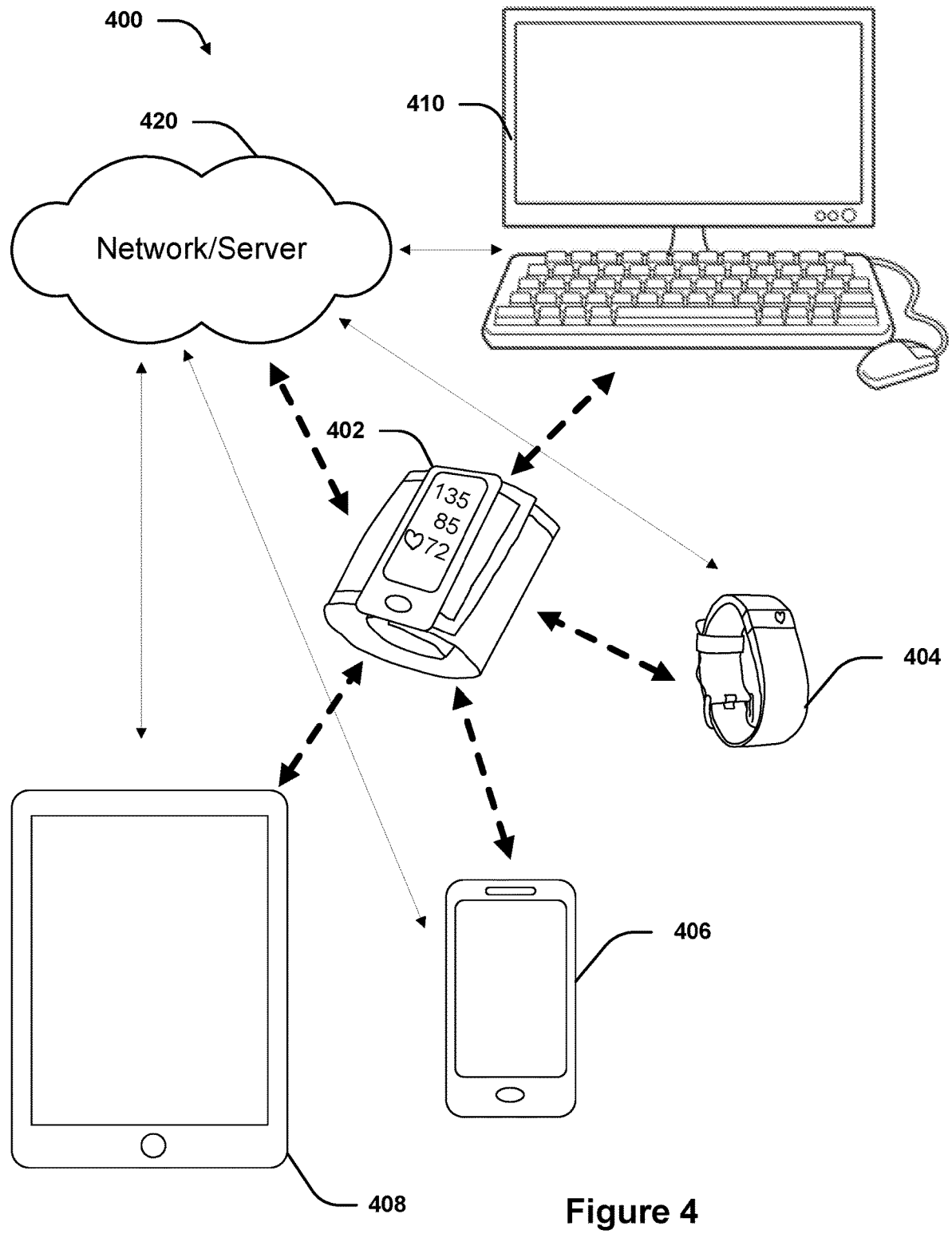
FIG. 4 shows a collection of devices that can be interconnected to each other and to a network of computers or servers.

As shown in FIG. 4, an IOBPM device 402 similar to the device 322 can connect to various secondary devices. The secondary devices may include a wearable biometric monitoring device 404, a mobile phone 406, a GPS device, set-top box, gaming console, a computer (e.g., a portable computer, a desktop computer 410, or a server computer in a network 420), or a tablet 408. The secondary devices may also include combinations of one or more of the above-mentioned devices. The communication links between the blood pressure device 402 and the second devices are indicated by thick dashed lines. FIG. 4 shows a collection of devices 400 that can be interconnected to each other and to a network of computers or servers 420. In some implementations, network 420 includes server computers that form a part of the Internet or a part of computing "cloud." In some implementations, the blood pressure measurement device 402 can send blood pressure data (or other biometric data) to one or more of the secondary device is to be processed and/or stored. In some implementations, network 420 includes an intranet. The blood pressure measurement device 402 can send blood pressure data to be processed and/or stored on a secondary device in the network 420 or "cloud." The connections between the secondary devices and network 420 are illustrated by thin dashed lines. Computer 410, biometric monitoring device 404, smart phone 406, and tablet 406 can establish connections among themselves even though are not illustrated here. As such, the blood pressure measurement device 102 can obtain and send information either directly or indirectly to secondary devices shown in the figure.

Figure 5:
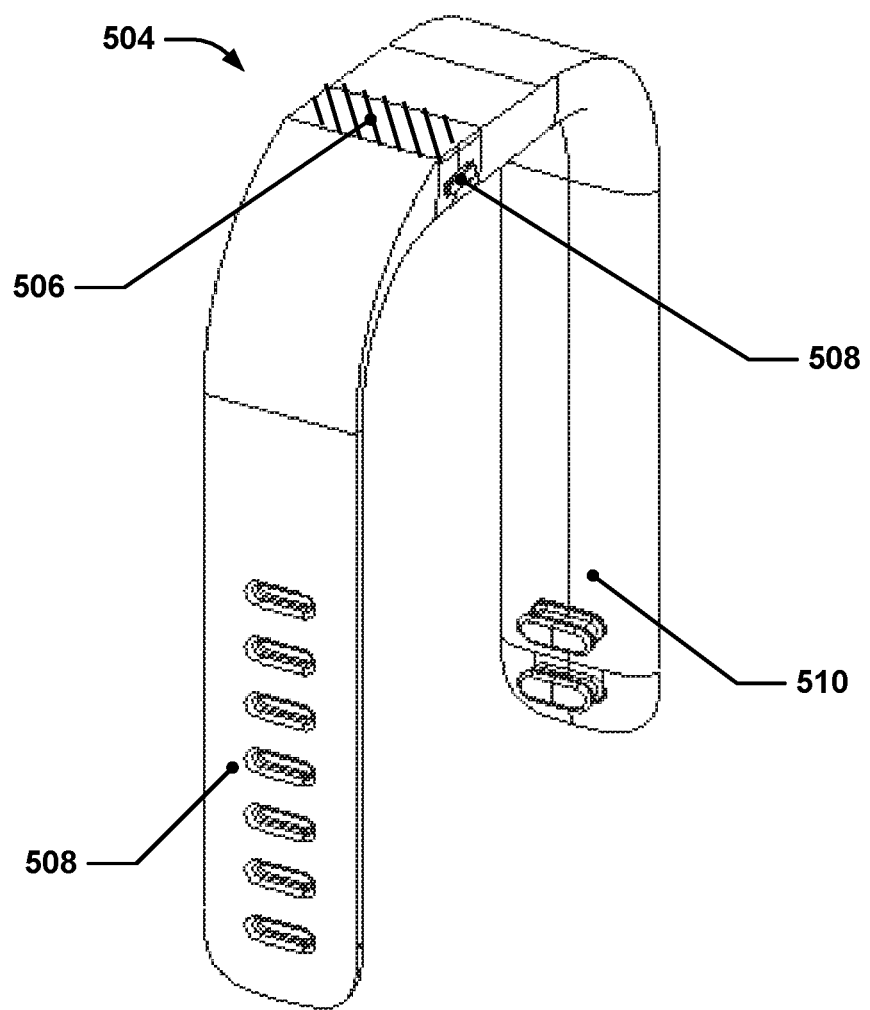
FIG. 5 shows a wearable biometric monitoring device involved in some implementations of the disclosure.

FIG. 5 shows a wearable biometric monitoring device 504 that is similar to the device 404 in FIG. 4. The wearable biometric monitoring device 504 is configured to be of a wristband shape that may be worn on the wrist. The biometric monitoring device 504 includes a wristband structure 510. Moreover, the biometric monitoring device 504 includes a display 506. Moreover, the device 504 includes a button that allows user interaction. In some implementations, the biometric monitoring device 504 includes biometric sensors; it can obtain biometric data generated by the biometric sensors; and it can analyze biometric data generated by the biometric sensors. Features and structures of biometric monitoring devices are described in U.S. Pat. No. 8,948,832, which is incorporated by reference in its entirety for all purposes. As described above and hereinafter, the biometric monitoring device 504 can exchange data with the blood pressure measurement device 402. In some implementations, the biometric monitoring device 504 can also analyze data obtained through the blood pressure measurement device 402. Conversely, in some implementations, data sent from the biometric monitoring device 504 to the blood pressure measurement device 402 can be analyzed by the blood pressure measurement device 402.

Biometric sensors that may be incorporated into the biometric monitoring device 504 are further described in the Biometric Sensor section hereinafter.

Automatic User Identification

Some implementations provide methods and devices for obtaining and storing blood pressure data, wherein the user's identification is automatically determined, which allows for effective management of user data and user-customized experience with blood pressure measurements. In various implementations, an intelligent oscillometric blood pressure measurement device and a second device are applied. The intelligent oscillometric blood pressure measurement device can exchange data with the second device through a wireless connection or a wired connection.

Figure 6:
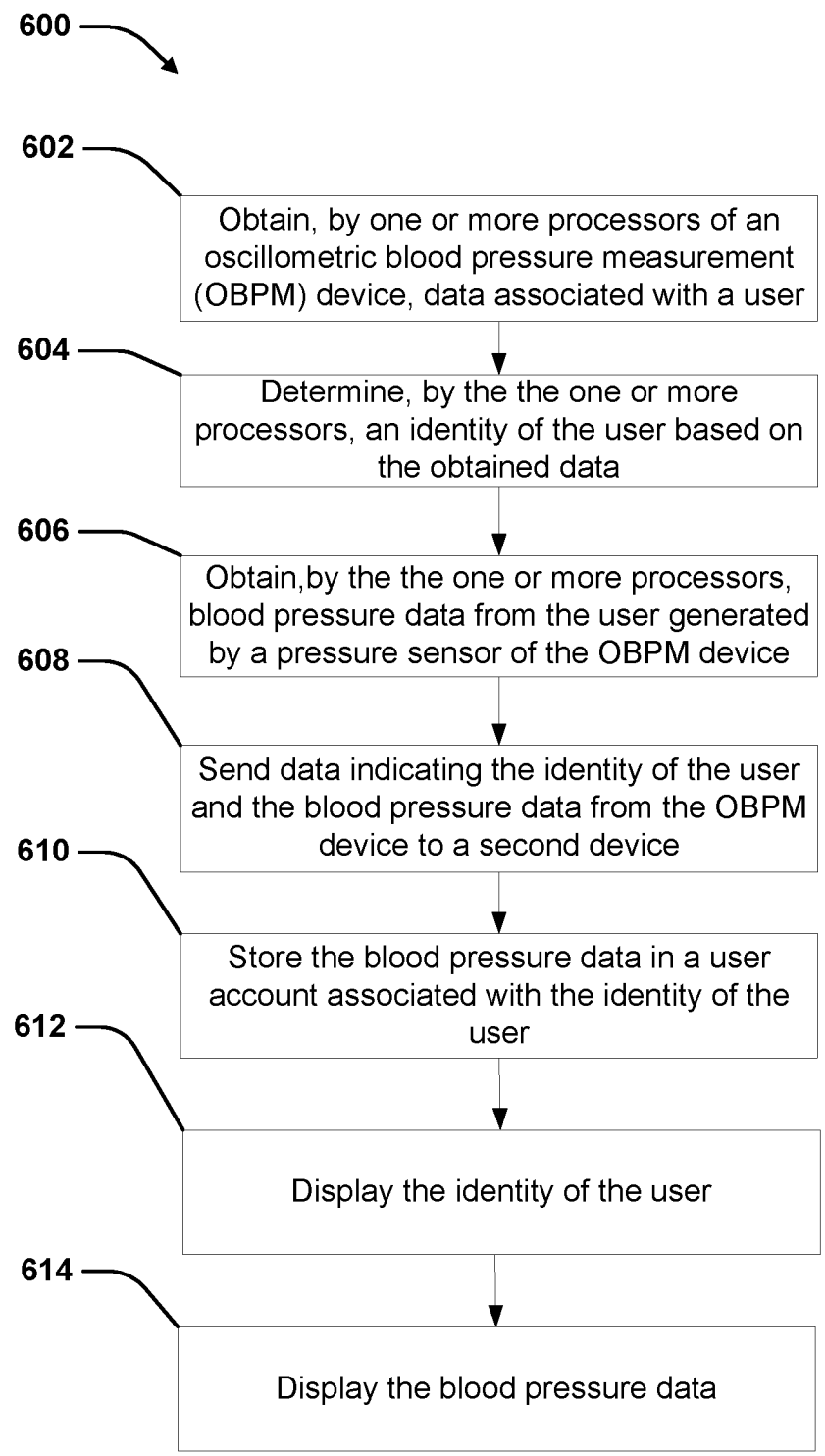
FIG. 6 shows a flowchart illustrating a process for obtaining and storing blood pressure data according to some implementations.

In some implementations, the intelligent oscillometric blood pressure measurement device can automatically determine the identity of the user from whom the pressure data are collected. FIG. 6 shows a flowchart illustrating process 600 for obtaining and storing blood pressure data according to such implementations. The intelligent oscillometric blood pressure measurement device includes an inflatable cuff, a pressure sensor, a communication circuitry, a memory, and one or more processors. The intelligent oscillometric blood pressure measurement device has the ability to communicate with a second device through the communication circuitry via a wireless communication protocol or a wired communication protocol. Process 600 first involves obtaining, by the one or more processors, data associated with the user. See block 602. In some implementations, the data associated with the user includes biometric data, e.g., motion data, ECG data, PPG data, blood pressure data, arm circumference data, by electrical impedance analysis (BIA) data, fingerprint sensor data, and the like.

Process 600 further involves determining, by the one or more processors, an identity of the user using the obtained data associated with the user. See block 604. In some implementations, determining the identity of the user involves providing the biometric data to a classifier to determine the identity of the user. In some implementations, the classifier takes a set of test biometric data and compares it to one or more sets of reference biometric data that are associated with one or more known users. For example, in some implantations, blood pressure data collected from the IOBPM is compared to that of a set of users and associated with the user with the closest blood pressure values.

The classifier then determines the test biometric data is associated with a particular user when the comparison result meets a criterion. In some implementations, the classifier determines the test biometric data is associated with the user that is most similar to the test biometric data. In some implementations, the one or more sets of reference data are recorded biometric data that are previously obtained from the one or more users, or biometric data derived therefrom (e.g., averaged data based on multiple previous sessions of data obtained from the same user). The currently tested biometric data and the previously obtained biometric data may be collected from either the same device or from different devices.

In other implementations, the one or more sets of reference data are not previously collected from the one or more users, but are assigned to the one or more users. For example, based on characteristics of users (e.g., age, gender, weight measurements), different reference data sets (e.g., reference heartbeat waveform data sets reference blood pressure data sets) can be assigned to different users. In some implementations, the one or more sets of reference data include biometric data concurrently collected from a known user using the second device. In some implementations, the test data and the reference data are time stamped. For instance, the intelligent oscillometric blood pressure measurement device may obtain heartbeat waveform data through a PPG sensor. Meanwhile, a second device such as wearable biometric monitoring device may also obtain heartbeat waveform data through a PPG sensor, where the identity of the user wearing the biometric monitoring device is known. The classifier can compare or cross correlate the heartbeat waveform data obtained by the intelligent oscillometric blood pressure measurement device and those obtained by the second device. Based on the similarity or the correlation of data obtained by the two devices, the classifier to determine whether the data match. If so, the classifier determines that the test heartbeat waveform data from the oscillometric blood pressure device is associated with the user.

In some implementations, the user classifier processes a test data set to obtain a data signature, e.g., a motion signature or a heartbeat waveform signature that are or tend to be user specific. The classifier then compares the obtained data signature to signatures that are associated with one or more users. The classifier finally determines a user identity associated with the test data based on the comparison of the obtained signature and signatures known to be associated with the one or more users. In some implementations, the user whose data signature is most similar to the test data signature is determined to be the user associated with the test data.

In some implementations, the classifier is trained by machine learning using data of a plurality of users. In some implementations, the machine learning involves supervised learning of the classifier. In some implementations, the classifier includes a neural network model. Supervised learning of a neural network model involves providing training data sets known to be associated with one or more users and adjusting strengths of neural connections of the neural network based on the accuracy of the prediction of user identities predicted by the neural network model. Then when a neural network classifier is used, a test data set is provided to the new network model, which then predicts the user identity.

In some implementations, the classifier includes a general linear model or a nonlinear model, where the models parameters are optimized to fit training data known to be associated with one or more users. Then when the linear or nonlinear classifier is used, the test data set may be analyzed to obtain parameter values, which are then compared to the parameters of the different users. The classifier can then determine a user identity comparison of the parameters.

In some implementations, the classifier is trained by unsupervised machine learning using training data sets of known users and applying techniques such as unsupervised clustering.

In other implementations, the data associated with the user includes nonbiometric data. In some implementations, the nonbiometric data includes data indicating that the intelligent oscillometric blood pressure measurement device is paired with the second device through a wireless communication protocol, such as a protocol of Wi-Fi, Bluetooth, NFC, infrared, ZigBee, etc. Based on the pairing of the two devices, the oscillometric a pressure measuring device determines the identity of the user. In some implementations, the second device is associated with the user via the hardware characteristic of the mobile device. For instance, a serial number or a network MAC address of the second device may be associated with the user. When the intelligent oscillometric blood pressure measurement device obtains data with information about the serial number or the MAC address, it can determine the user's identity. In some implementations, the second device is the closest connectable device as measured by received signal strength indicator (RSSI), which is a measurement of the power present in a received radio signal.

In some implementations, the data obtained by the one or more processors include the user input specifying the identity of the user. This information may be used to supplement other data when the one or more processors cannot determine the user identity or cannot determine the user identity with sufficient confidence using the other data.

In some implementations, the data obtained by the one or more processors include data generated by one or more sensors of the intelligent oscillometric blood pressure measurement device. In some implementations, the data obtained by the one or more processors include data that are generated on the second device and obtained through the communication circuitry of the intelligent oscillometric blood pressure measurement device.

In some implementations, an IOBPM can be connected to a wearable biometric monitoring device or a phone. The wearable biometric monitoring device or the phone is associated with the identity of a user (e.g., the owner) via one or more data described above. When the connection between the IOBPM and the wearable biometric monitoring device or phone is established, blood pressure data obtained by the IOBPM is identified as being associated with the user.

In some implementation, a system includes a biometric monitoring device that can obtain data about heart rate, step count, date or time stamped heart beat waveform, respiration rate or interval, and the like. The biometric monitoring device and the data obtained therefrom are associated with a user. The system also includes an IOBPM that provides blood pressure data and optionally other biometric data. The blood pressure data or the other biometric data from the IOBPM can be compared to the data from the biometric monitoring device, e.g., by using one or more of the classifiers described above. When data from the IOBPM match that from the biometric monitoring device, the blood pressure data is determined to be obtained from the user associated with the biometric monitoring device.

Process 600 further involves obtaining blood pressure data from the user using the oscillometric blood pressure measuring device. See block 606. Process 600 includes sending data indicating the identity of the user in the blood pressure data to a second device through the communication circuitry of the intelligent oscillometric blood pressure measurement device. See block 608.

In some implementations of the disclosure as shown here, process 600 also involves storing the blood pressure data in a user account associated with the identity of the user. See block 610. In some implementations, the blood pressure data is stored on the second device. In other implementations, the blood pressure data is sent to a network storage device over a network such as a cloud storage device.

In some implementations, process 600 also includes displaying the identity of the user. See block 612. In some implementations, the intelligent oscillometric blood pressure measurement device also includes a user interface. Operation 612 involves displaying the identity of the user or information derived therefrom (e.g., first name, last name, initials, alias, nickname, avatar, etc.) on the user interface of the intelligent oscillometric blood pressure measurement device. In some implementations, the second device includes a user interface. Operation 612 involves displaying the identity of the user or information derived therefrom on the user interface of the second device.

Figure 7:
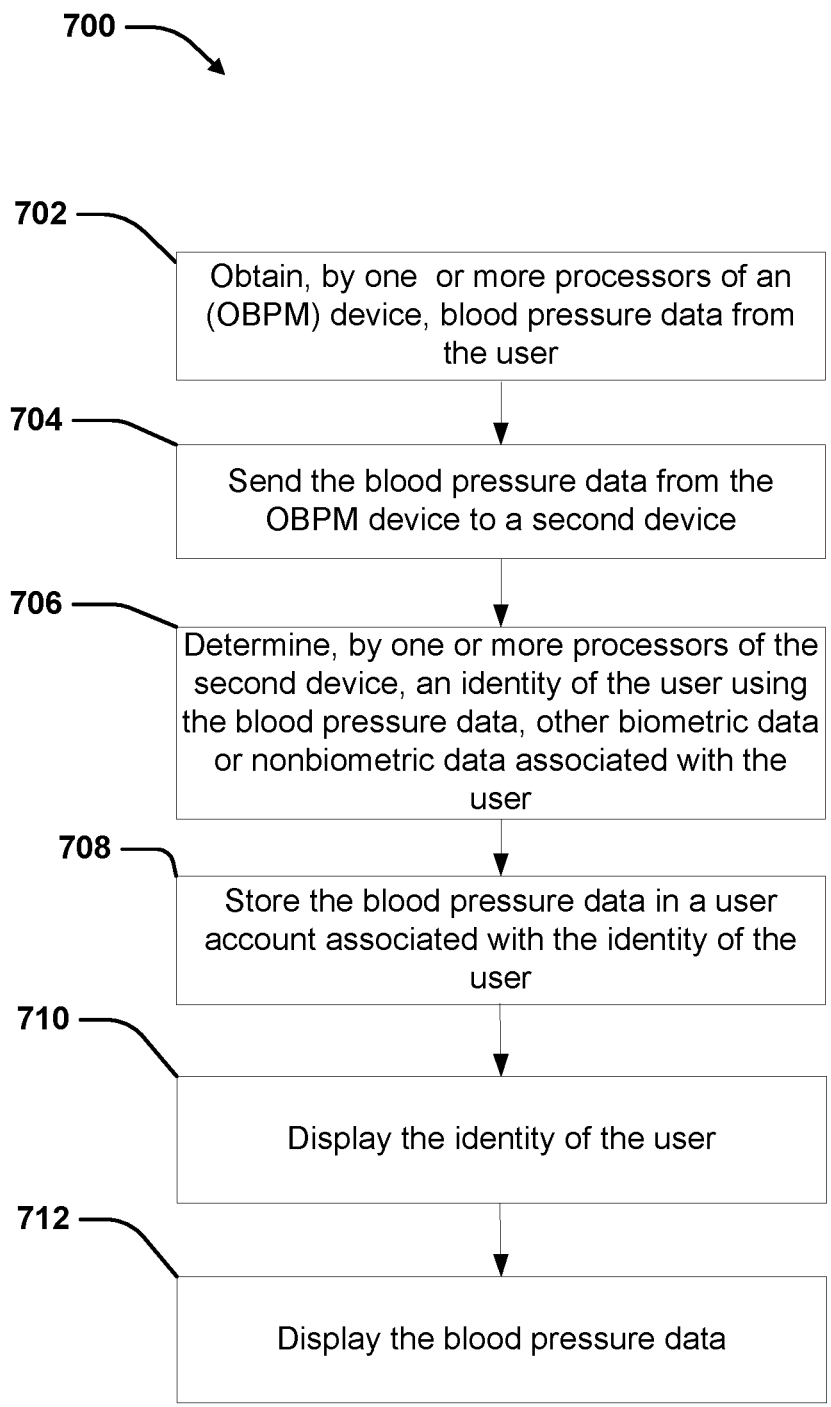
FIG. 7 shows a flowchart illustrating another process for obtaining and storing blood pressure data according to some implementations.

In some implementations, the second device can automatically determine the identity of the user from whom the blood pressure data are collected. FIG. 7 shows a flowchart illustrating process 700 for obtaining and storing blood pressure data according to such implementations. The second device includes a memory, second communication circuitry, and one or more processors. Process 700 first involves obtaining, by the intelligent oscillometric blood pressure measurement device, blood pressure data generated by the pressure sensor from a user. See block 702. Process 700 and involves sending the pressure data from the oscillometric blood pressure measuring device to the second device, which involves communication between the first communication circuitry of the oscillometric blood pressure measuring device and the second communication circuitry of the second device. See block 704. Process 700 further includes determining, by the one or more processors of the second device, an identity of the user using the blood pressure data, other biometric data associated with the user, the nonbiometric data associated with the user. See block 706.

In some implementations, determining the identity of the user associated with the blood pressure data includes providing the blood pressure data to a classifier to determine the identity of the user. Various classifiers described above in connection with block 604 can be used to determine the identity of the user here. In some implementations, determining the identity of the user includes obtaining from the user the other biometric data, and providing the other biometric data to a classifier to determine the identity of the user. In some implementations, the second device includes one or more biometric sensors, and the other biometric data includes data generated by the one or more biometric sensors of the second device. In some implementations, the biometric blood pressure measurement device includes one or more additional biometric sensors in addition to the pressure sensor. The other biometric data includes data generated by the one or more additional biometric sensors of the intelligent oscillometric blood pressure measurement device, the data being obtained through the communication between the first communication circuitry and the second communication circuitry. In some implementations, the other biometric data includes motion data, ECG data, PPG data, blood pressure data, arm circumference data, BIA data, fingerprint sensor data, and the like.

In some implementations, the nonbiometric data associated with the user a similar to the nonbiometric data described above in connection with block 604.

In some implementations, process 700 further involves storing the blood pressure data in an account associated with the identity of the user, see block 708, which is similar to operation 610 described above. In some implementations, process 700 also involves displaying the identity of the user and displaying the blood pressure data, blocks 710 and 712, which are performed similar to operations 6612 and 614 described above.

Automatic Instructions for Taking BP Measurements

Figure 8:
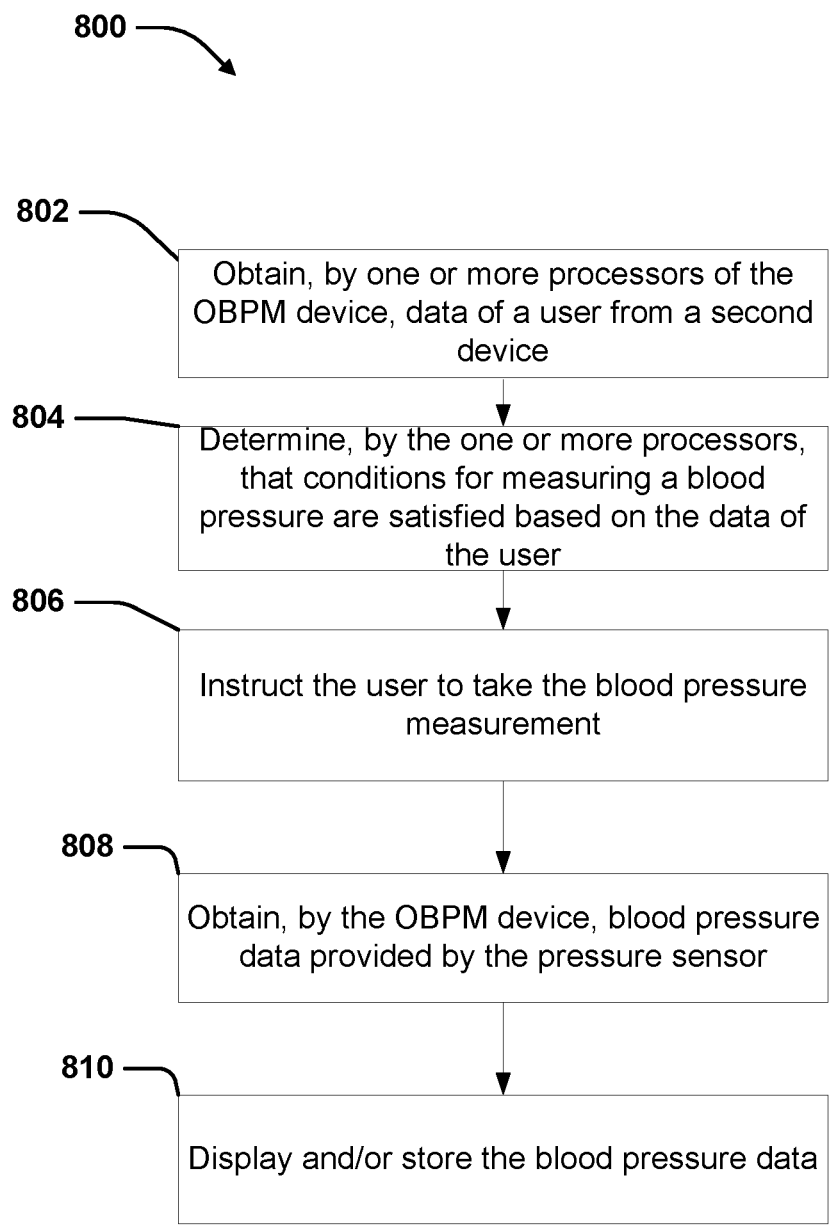
FIG. 8 shows a flowchart illustrating a process for measuring blood pressure using a blood pressure measurement device that has the ability to automatically provide instructions based on user conditions that are relevant to quality of blood pressure measurements.

FIG. 8 shows a flowchart illustrating a process 800 for measuring/estimating blood pressure using a blood pressure measurement device that has the ability to automatically provide instructions based on user conditions that are relevant to quality of blood pressure measurements. The process is implemented using an intelligent oscillometric blood pressure measurement device that can connect to a second device. The intelligent oscillometric blood pressure measurement device includes an inflatable cuff, a pressure sensor, communication circuitry, and one or more processors communicatively linked to the pressure sensor and the communication circuitry. Process 800 first involves receiving, via the communication circuitry, data of the user from the second device. See block 802. In some implementations, the data of the user includes biometric data. In some implementations, the second device includes one or more biometric sensors configured to collect the biometric data, and the biometric data involved in process 800 a collected from the one or more biometric sensors. In some implementations, the biometric data includes data about one or more of the following: sleeping, waking, heart rate or heartbeat waveform, amount and composition of food consumption, motion, activity, and the like. In some implementations, the second device includes a wearable device one by the user. In some implementations, the wearable device is configured as a wrist worn device such as device 404 or device 405. In some implementations, the second device includes a smart phone.

Process 800 proceeds to determine, by the one or more processors of the intelligent oscillometric blood pressure measurement device, conditions for measuring a blood pressure are satisfied based on the data of the user. See block 804. In some implementations, the conditions for measuring the blood pressure are selected from one or more of the following: having no recent exercises or steps, having no erratic motions, physiological stress, or elevated heart rate, having low heart rate variability, not having recently consumed food or drugs, having recently ended a commute, having recently waken up, approaching the usual sleeping time of the user, and the like. In some implementations, the conditions for measuring the blood pressure a selected from one or more of the following: having recent exercises or steps, having physiological stress or elevated heart rate, having high heart rate variability, having recently consumed food or drugs.

Process 800 further involves instructing the user to take a blood pressure measurement. See block 806. In some implementations, the IOBPM device includes a user interface. Instructing the user involves: displaying a visual instruction or visual cue through the user interface, playing an auditory instruction or auditory cue through the user interface, vibrating the IOBPM device, etc. In some implementations, instructing the user involves: sending the instruction to the second device, and providing the instruction by using the second device, which may involve displaying a visual instruction or visual cue by using the second device, playing an auditory instruction and/or auditory cue by using the second device, vibrating the second device, etc.

Process 800 further involves obtaining blood pressure using the one or more processors and the pressure sensor of the symmetric blood pressure measurement device. See block 808. In some imitations, the process also includes displaying and or storing blood pressure data as described above for process 600 and process 700. See block 810.

Intelligent Inflation of Cuff

Figure 9:
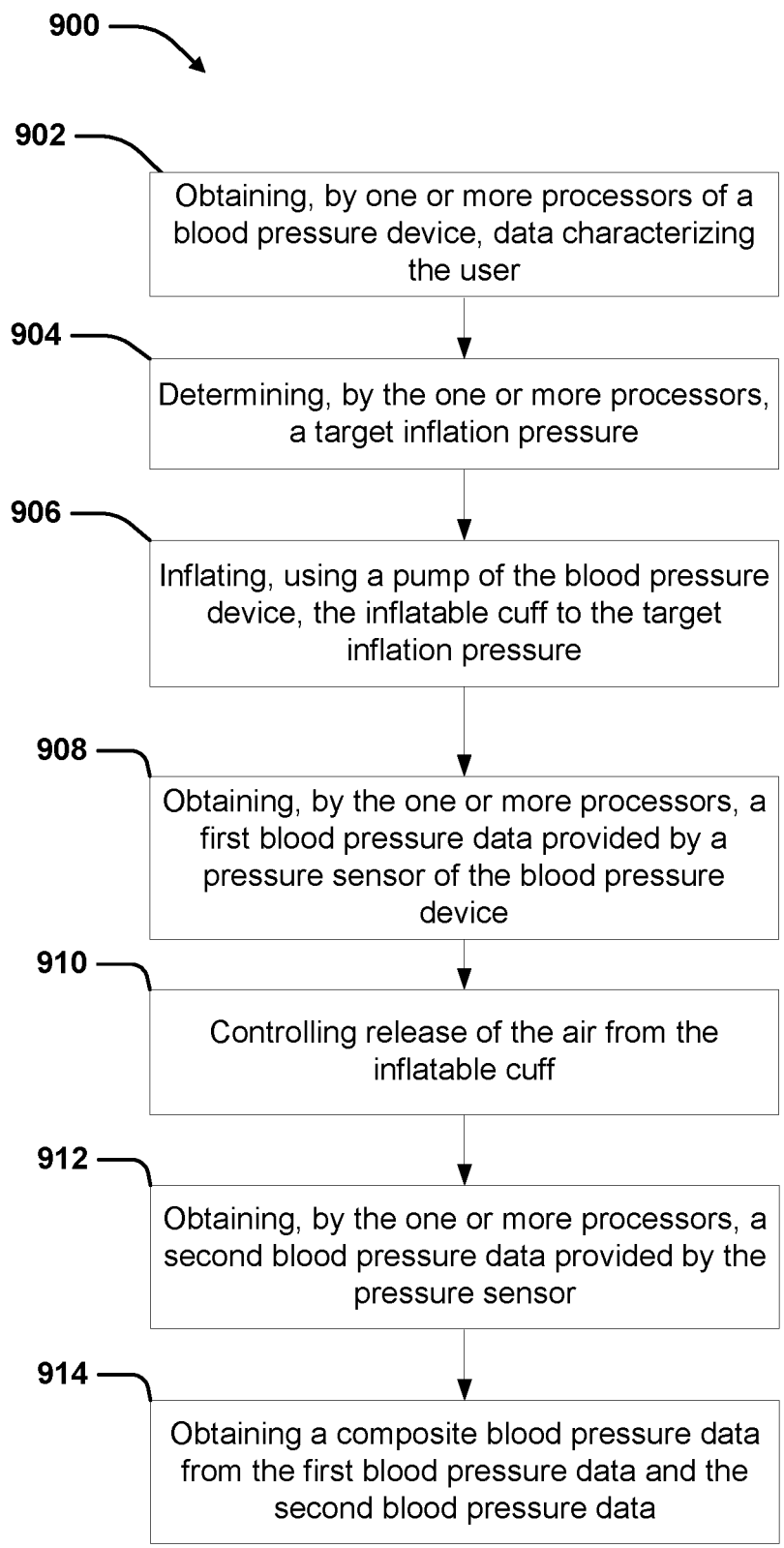
FIG. 9 shows a process for measuring blood pressure using an inflatable cuff according to some implementations.

FIG. 9 shows a process 900 for measuring blood pressure using an inflatable cuff according to some implementations. Process 900 involves intelligently inflating the inflatable cuff, thereby providing a more comfortable user experience and improving measurement speed without sacrificing measurement accuracy. Process 900 is implemented using a blood pressure device including an inflatable cuff, the pressure sensor, a pump, and one or more processors communicatively linked to the pressure sensor and the pump. In some implementations, the blood pressure device includes an oscillometric the pressure measurement device. Process 900 starts by obtaining by the one or more processors data characterizing the user. See block 902. In some implementations, the data characterizing the user include biometric data. In some implementations, the biometric data are generated by one or more biometric sensors of the blood pressure device. In some implementations, the data characterizing the user included demographic data of the user, such as age, gender, height, weight and information related thereof, etc.

Process 900 further involves determining, by the one or more processors, a target inflation pressure. See block 904. In some implementations, determining the target inflation pressure based on the data characterizing the user includes: determining, by the one or more processors, an identity of the user based on the data characterizing the user; accessing one or more stored blood pressure values linked to the identity of the user; and determining the target inflation pressure relative to the one or more stored pressure values. In some implementations, the one or more stored blood pressure values include blood pressure values, e.g., systolic pressure values, previously obtained from the user. In some implementations, the target inflation pressure is set to be a certain percentage or a criterion above the previously recorded systolic pressure values. In other implementations, the one or more stored blood pressure values are associated with or assigned to the user based on one or more user characteristics, such as age, gender, weight measurements, and the like. In some implementations, determining the identity of the user involves providing the data to a classifier to determine the identity of the user. In some implementations, the blood pressure device also includes communication circuitry, and accessing the one or more stored blood pressure values includes obtaining the one or more stored blood pressure values from a second device via the communication circuitry.

In some implementations, determining the target inflation pressure involves: calculating, when inflating the cuff, estimates of systolic and/or diastolic pressure of the user, and calculating, by the one or more processors, a target pressure using the estimates of systolic and/or diastolic pressure. For instance, in some implementations, if the inflatable cuff is being inflated and pressure data is being obtained, the pressure data may be processed on the fly to obtain an estimate of systolic pressure. Meanwhile, the target inflation pressure may be set to be a percentage or a criterion value above the systolic pressure, which may be lower than a fixed preset value.

In some implementations, determining the target inflation pressure involves: using a PPG sensor placed distal to the center of the inflatable pressure cuff to detect a cessation or near cessation of the pulse; and determining the target inflation pressure relative to a pressure of the inflatable cuff when the cessation or near cessation of the pulse is detected.

Process 900 further involves inflating, using the pump of the blood pressure device, the inflatable cuff to the target inflation pressure. See block 906.

Process 900 also involves obtaining, by the one or more processors, blood pressure data provided by the pressure sensor of the blood pressure device. See block 908.

Figure 10:
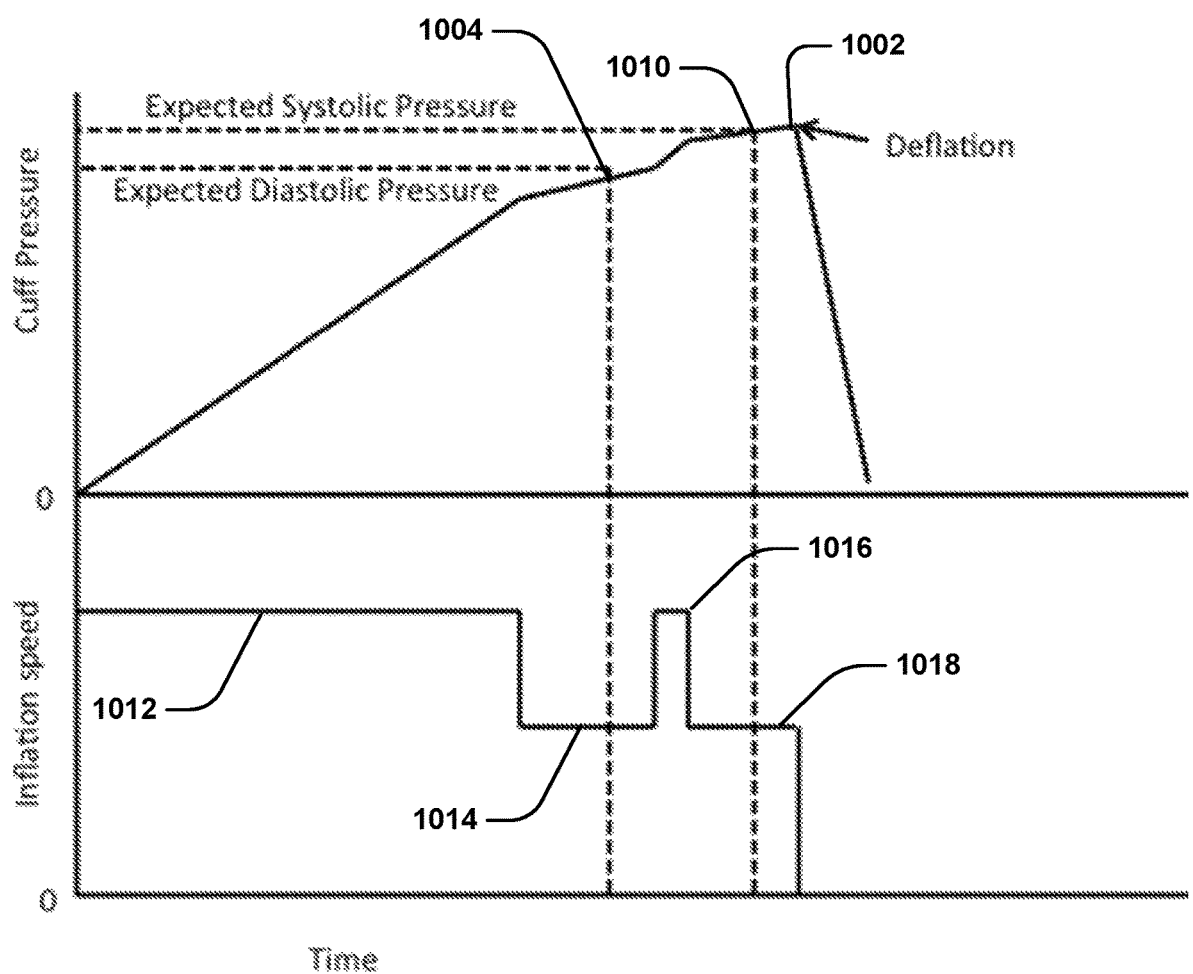
FIG. 10 illustrates cuff pressure as functions of time and corresponding variable inflation speeds according to some implementations.

In some implementations, inflating the inflatable cuff to the target inflation pressure involves a variable inflation speed profile such as that shown in the bottom half of FIG. 10. FIG. 10 illustrates cuff pressure as functions of time and corresponding variable inflation speeds according to some implementations. The top half of FIG. 10 shows cuff pressure is a function of time. A target inflation pressure appears at 1002, which is higher than expected systolic pressure appearing at 1010. Expected diastolic pressure is at 1004 on the pressure curve. As shown here, the cuff pressure in the top half of the figure increases quickly when the pressure is far away from the expected diastolic pressure or the expected systolic pressure. The bottom half of FIG. 10 shows the variable inflation speed profile, which has a higher speed at sections 1012 and 1016, because the corresponding time periods are relatively remote from the expected diastolic pressure and the expected systolic pressure. This helps to reduce the total amount of time required to reach the target pressure. On the other hand, the cuff pressure in the top half of the figure, the pressure change slows down when the pressure approaches the expected diastolic pressure or the expected systolic pressure. The variable inflation speed profile in the bottom half of the figure has a lower speed at sections 1014 and 1018, because the corresponding time periods are relatively close to the expected diastolic pressure and the expected systolic pressure. This helps to slow down cuff pressure change, thereby allowing more time to obtain pressure oscillation data, which helps to improve data quality and analysis accuracy. In some implementations, process control techniques such as proportional—integral—derivative control (PID control) may be used to create the desired pressure profile using a pressure sensor and a variable speed cuff pump. These more advanced control techniques can account for the variance in tightness with which a user may apply the blood pressure cuff, which can affect the pump speed to cuff pressure relationship.

In some implementations, the expected personal pressure and expected systolic pressure may be calculated based on the identity of the user. In some implementations, the process involves determining the identity of the user. In some implementations, the process further involves obtaining biometric data collected from the user, and determining the identity of the user based on biometric data collected from the user.

In some implementations, before the inflatable cuff is inflated to the target inflation pressure, the method includes inflating a pre-inflation bladder to a pre-inflation pressure higher than atmospheric pressure; and releasing air from the pre-inflation bladder to the inflatable cuff. In some implementations, the inflatable cuff can initiate inflation of the pre-inflation bladder before the inflation cuff applies pressure on the user. After the inflation cuff has been properly placed for measuring blood pressure, the air from the pre-inflation bladder can be quickly released and transferred to the inflation bladder, speeding up the time it takes to fully inflate the inflation bladder. In some implementations, the pre-inflation pressure is based at least in part on the target inflation pressure. In some implementations, the pre-inflation pressure is based at least in part on an expected diastolic pressure of the user. In some implementations, the pre-inflation pressure is calculated such that the air released from the pre-inflation bladder when released into the inflation bladder will inflate the inflation bladder to a pressure lower than the expected diastolic pressure by a particular degree, e.g., 10% lower than the expected diastolic pressure. This will quickly inflate the inflation bladder to the pressure lower than the expected diastolic pressure. Then a lower inflation speed may be applied when the cuff pressure approaches or is near the diastolic pressure.

Figure 12:
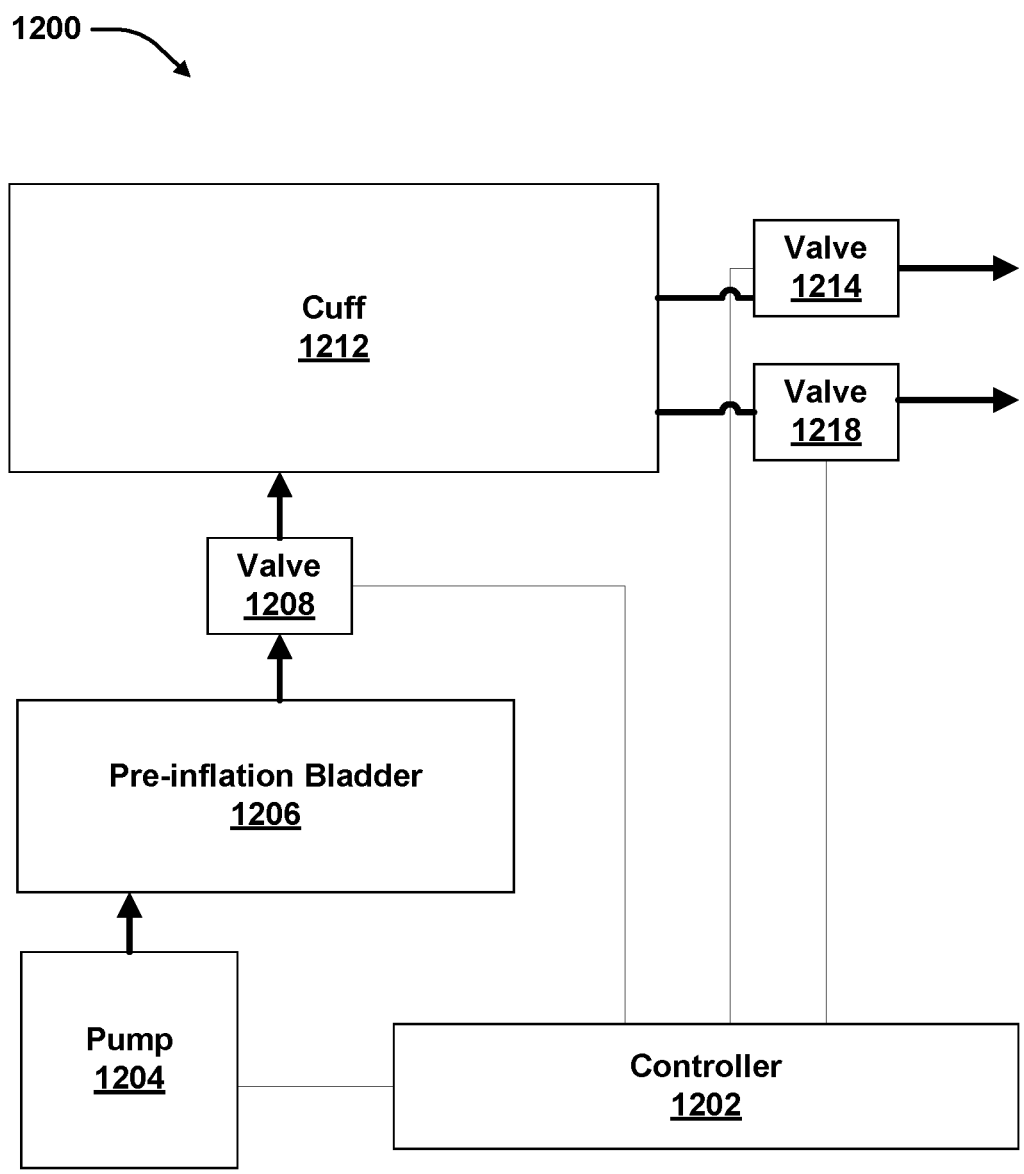
FIG. 12 shows a block diagram of a blood pressure cuff device including an inflatable cuff and a pre-inflation bladder.

FIG. 12 shows a block diagram of a blood pressure cuff device 1200 including an inflatable cuff 1212 and a pre-inflation bladder 1206, which can be used to implement the pre-inflation operations described above. The blood pressure cuff device 1200 also includes a pump 1204. Moreover, the device 1200 also includes a valve 1208 that regulates the flow between the prefilled bladder 1206 and the inflatable cuff 1212. Moreover, the device also includes available 1214 and a valve 1218 that regulate release of air from the cuff 1212. The pump 1204, valve 1208, valve 1214 and valve 1218 or controlled by the controller 1202. The controller 1202 can activate the pump 1204 and closes the valve 1208 before the cuff 1212 starts applying pressure on a user, thereby storing air in the pre-inflation bladder 1206, which stored air may be quickly released to from the pre-inflation bladder 1206 by opening valve 1208 when the cuff 1212 needs to be quickly inflated to obtain pressure data.

Valve 1214 and valve 1218 of device 1200 may be controlled by the controller 1202 to allow different deflation speed. For instance, opening only valve 1214 allows a slow deflation speed, opening only valve 1218 allows a faster deflation speed, and opening both valve 1214 and valve 1218 allows the fastest deflation speed.

In some implementations, process 900, after the inflatable cuff is inflated to the target inflation pressure, controlling the release of air from the inflatable cuff (e.g., deflating slowly), e.g., block 910, and obtaining blood pressure data before and after the inflatable cuff is inflated to the target inflation pressure. See block 912. In some implementations, process 900 also includes calculating a composite blood pressure value (e.g., an average or weighted average) using the blood pressure data obtained before and the blood pressure data obtained after the inflatable cuff is inflated to the target inflation pressure. See block 914. In some implementations, the composite blood pressure value is an average weighted according to the confidence of estimated blood pressure values or the quality of the blood pressure data. In some implementations, measurement during deflation may only occur when blood pressure measurement data during inflation meets at least one condition. For example, if accelerometer or pressure profile data during the inflation stage indicates movement of the user during inflation, measurement during deflation may be triggered. More generally, if data measured during inflation indicates that the blood pressure estimate may be non-optimal, measurement during deflation may be triggered. The user may also be cued that a second deflation measurement will occur and that they should match a state that will yield an accurate blood pressure estimate (e.g., not move).

Figure 11:
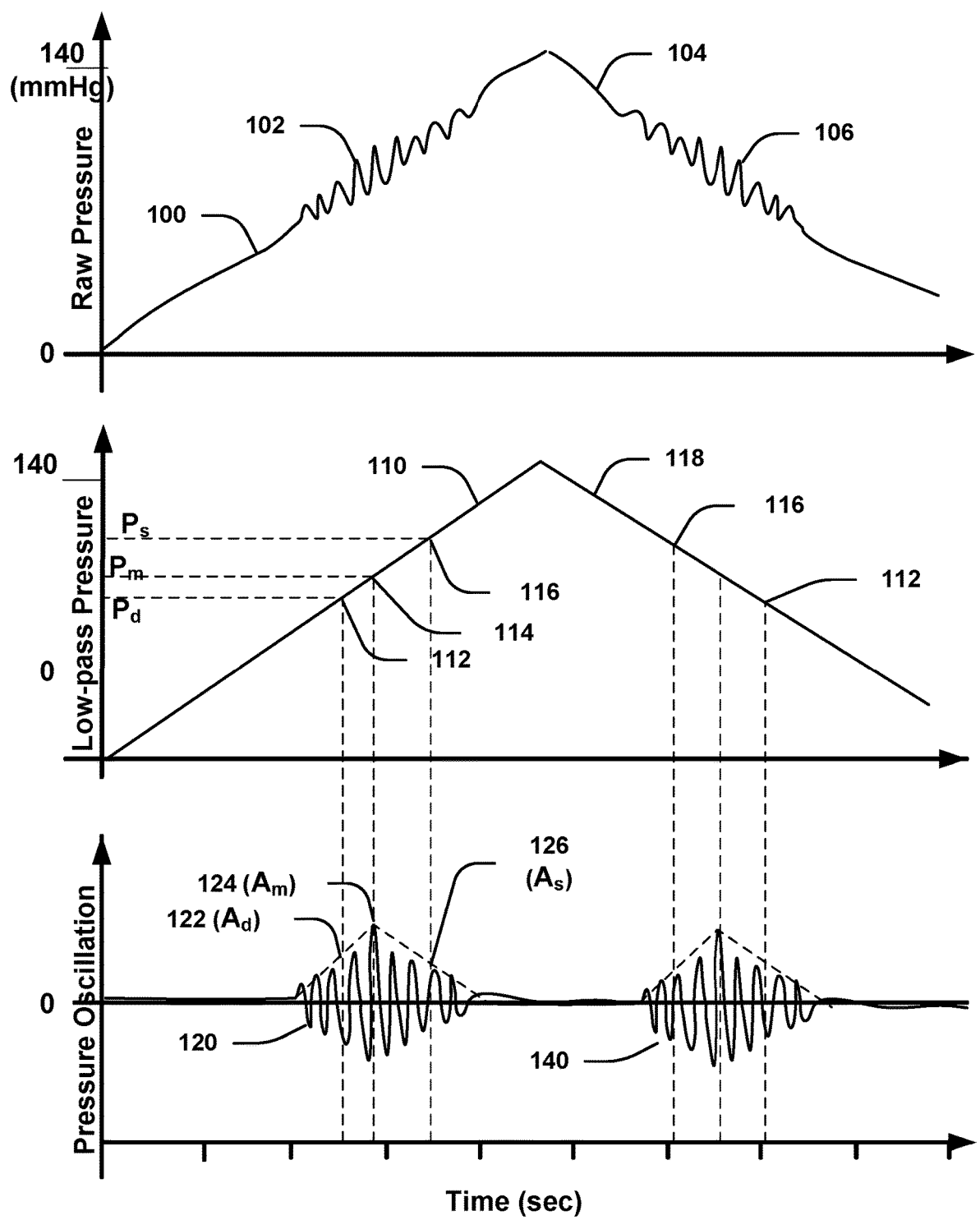
FIG. 11 shows schematic pressure data illustrating that oscillation data may be obtained during cuff deflation as well as during cuff inflation.

FIG. 11 shows schematic pressure data illustrating that oscillation data may be obtained during cuff deflation as well as during cuff inflation. Data in FIG. 1 is identical to data shown on the left half of FIG. 11. Raw external pressure data is shown in the top panel. As the pressure cuff deflates gradually, external pressure measurable by pressure sensor starts to decrease (104). As the external pressure continues to drop as it approaches systolic pressure, pressure oscillation occurs (106 and 134). Using the same principle during the inflation phase, diastolic pressure at 112 and systolic pressure at 116 can be estimated from oscillation data 140. In some implementations, the algorithm used in the inflation phase has different parameter values from the algorithm used in the deflation phase.

Improve Blood Pressure Estimate Using Non-Pressure Data

One aspect of the disclosure provides means to improving blood pressure estimate by using biometric data other than pressure data. In some embodiments, a process for estimating blood pressure is implemented using a IOBPM device including an inflatable cuff, a pressure sensor, at least one other biometric sensor, and one or more processors communicatively linked to the pressure sensor and the at least one other biometric sensor. In some implementations, the method includes: inflating the inflatable cuff to an inflation pressure; obtaining, by the one or more processors, pressure data provided by the pressure sensor; obtaining other biometric data provided by the at least one other biometric sensor; and estimating a blood pressure value using the pressure data and the other biometric data.

In some implementations, the at least one other biometric sensor includes one or more of the following: inertial sensors, acoustic sensors, electrocardiogram (ECG) sensors, photoplethysmograph (PPG) sensors, etc. In some implementations, the other biometric data include motion data and wherein estimating a blood pressure value involves using the motion data to reject motion artifacts from the pressure data. In some implementations, using the motion data to reject motion artifacts from the pressure data involves: identifying a motion component from the motion data, identifying a pressure component corresponding to the motion component, and removing the pressure component from the pressure data.

Figure 13:
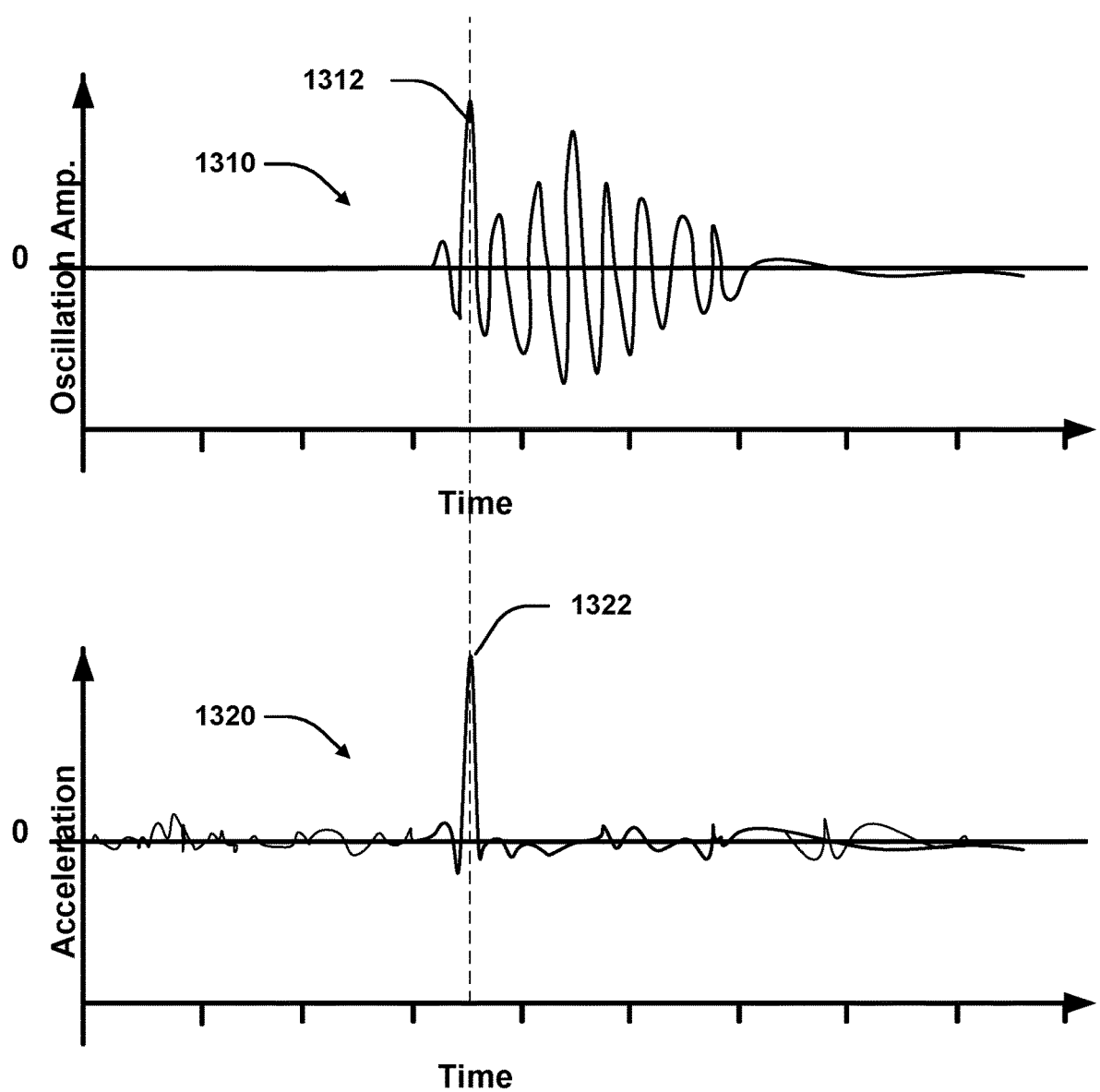
FIG. 13 illustrate schematic data that can be used by some implementations of the disclosure to remove motion artifacts of oscillation data using motion data.

FIG. 13 shows cartoons of schematic data that can be used by some implementations of the disclosure to remove motion artifacts from oscillation data using motion data. Pressure oscillation data 1310 is shown in the top half of FIG. 13, and acceleration data 1320 is shown in the bottom half of FIG. 13. In some implementations, the intelligent oscillometric blood pressure measurement device can obtain both pressure oscillation data and the acceleration data. Because pressure oscillation data are susceptible to motion artifact, oscillation data can be distorted by motion. By simultaneously obtaining oscillation data and acceleration data, motion components, such as motion signals spike 1322 coincides in time with oscillation change of 1312, indicating that motion underlies data variation reflected by both 1312 and 1322. In some implementations, a motion data component such as data having acceleration amplitude above a threshold is identified. See, e.g., motion data of 1322. An oscillation component corresponding to the motion component based on time is identified. See, e.g., oscillation data of 1312. Then the identified oscillation data component is removed from analysis of blood pressure.

In some implementations, the other biometric data other than blood pressure data are generated by the intelligent oscillometric blood pressure measurement device. In other implementations, the other biometric data are generated by a second device.

In some implementations, the other biometric data includes PPG sensor data. PPG sensor data may be time with oscillation data. Then one or more periodic PPG components can be identified in the PPG sensor data. The periodic PPG components can be used to identify corresponding oscillation periodic components that are otherwise difficult to identify using the oscillation data per se, where the oscillation periodic components, such as oscillation peaks, can be used to perform analysis to determine blood pressure values.

In some implementations, the other biometric data includes inertial data generated from an inertial sensor at the inflatable cuff, and wherein estimating the blood pressure value includes: obtaining orientation or placement information of the inflatable cuff using the inertial data; selecting parameter values based on the orientation or placement information; and calculate one or more blood pressure values using the pressure data and the selected parameter values.

In some implementations, the relation between the orientation or placement information and suitable parameter values determined from training data. Then at test data of orientation or placement can be applied to the determined relation.

In other implementations, training data including orientation or placement information, as well as oscillation data, are provided to build a model to predict blood pressure values. Then test data including orientation or placement data, as well as oscillation data, are applied to the model to obtain blood pressure values.

The above approaches account for orientation or placement information, and do not necessarily require blood pressure measurements to be taken with specific orientation or placement. In some implementations, the device has the capability to automatically instruct the user to adjust a placement or an orientation of the inflatable cuff when the obtained orientation or placement information indicates an improper orientation or placement. This instructing approach may be used to improve accuracy when orientation or placement of the device cannot be adequately removed by analytical approach alone.

In some implementations, the other biometric data includes inertial data generated from an inertial sensor, and wherein estimating the blood pressure value includes: determining a posture of the use using the inertial data; selecting parameter values based on the posture; and calculating one or more blood pressure values using the pressure data and the selected parameter values.

In some implementations, estimating the blood pressure value includes: determining posture data of the use using the inertial data; applying the posture data and the pressure data to a model to obtain one or more blood pressure values.

Biometric Sensors

In some embodiments, the blood pressure measurement device (e.g., 402) or the biometric monitoring device (e.g., 404) includes a heart rate sensor that detects electrical signal generated by heart movement (e.g., electrode sensor) or an optical signal resulting from blood flow (e.g., photoplethysmography sensor or pulse oximetry sensor). In addition to heart rate data, the blood pressure measurement devices or the biometric monitoring devices discussed herein may collect one or more types of physiological and/or environmental data from sensors embedded within the blood pressure measurement devices or the biometric monitoring devices, e.g., one or more sensors selected from the group including accelerometers, gyroscopes, altimeters, etc., and/or external devices, e.g., an external blood pressure monitor, and may communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device may then transmit the data representative of the user's step count to an account on a web service, e.g., Titbit dot com, a computer, a mobile phone, or a health station where the data may be stored, processed, and visualized by the user. Indeed, the device may measure or calculate a plurality of other physiological metrics in addition to, or in place of, the user's heart rate.

The measured physiological metrics may include, but are not limited to, energy expenditure, e.g., calorie burn, floors climbed and/or descended, heart rate, heart rate variability, heart rate recovery, location and/or heading, e.g., via GPS, elevation, ambulatory speed and/or distance traveled, swimming lap count, bicycle distance and/or speed, blood pressure, blood glucose, skin conduction, skin and/or body temperature, electromyography data, electroencephalography data, weight, body fat, caloric intake, nutritional intake from food, medication intake, sleep periods, sleep phases, sleep quality and/or duration, pH levels, hydration levels, and respiration rate. The device may also measure or calculate metrics related to the environment around the user such as barometric pressure, weather conditions, e.g., temperature, humidity, pollen count, air quality, rain/snow conditions, wind speed, light exposure, e.g., ambient light, UV light exposure, time and/or duration spent in darkness, noise exposure, radiation exposure, and magnetic field. Furthermore, the blood pressure measurement device or the biometric monitoring device, or an external system receiving data from the blood pressure measurement device or the biometric monitoring device, may calculate metrics derived from the data collected by the blood pressure measurement device or the biometric monitoring device. For instance, the device may derive one or more of the following from heart rate data: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate. Some of the derived information is based on both the heart rate information and other information provided by the user (e.g., age and gender) or by other sensors (elevation and skin conductance).

The biometric sensors may include one or more sensors that evaluate a physiological aspect of a wearer of the device, e.g., heart rate sensors, galvanized skin response sensors, skin temperature sensors, electromyography sensors, etc. The biometric sensors may also or alternatively include sensors that measure physical environmental characteristics that reflect how the wearer of the device is interacting with the surrounding environment, e.g., accelerometers, altimeters, GPS devices, gyroscopes, etc. All of these are biometric sensors that may all be used to gain insight into the activities of the wearer, e.g., by tracking movement, acceleration, rotations, orientation, altitude, etc.

A list of potential biometric sensor types and/or biometric data types is shown below in Table 1, including heart rate sensors. This listing is not exclusive, and other types of biometric sensors other than those listed may be used. Moreover, the data that is potentially derivable from the listed biometric sensors may also be derived, either in whole or in part, from other biometric sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

Biometric Sensors and Data (physiological and/or environmental)

| Biometric Sensor Type | Biometric data potentially measured | Potentially derivable biometric data |
|---|---|---|
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation, angular velocity, angular acceleration and/or rotation | Rotation, orientation |
| Altimeters | Barometric pressure, temperature (to calculate a more accurate altitude) | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS) | Location, elevation, speed, heading | Distance traveled, velocity/speed |
| Electromyography Sensors | Electrical pulses | Muscle tension/extension |
| Audio Sensors | Local environmental sound levels | Laugh detection, breathing detection, snoring detection, respiration type (snoring, breathing, labored breathing, gasping), voice detection, typing detection |
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit ARIA ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as ARIA ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

In addition to the above, some biometric data may be calculated by the blood pressure measurement device or the biometric monitoring device without direct reference data obtained from the biometric sensors. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user and then used, in conjunction with data from an internal clock indicating the time of day, to determine how many calories have been expended by a person thus far in the day just to provide energy for basic bodily functions.

Physiological Sensors

As mentioned above, some biometric sensors can collect physiological data, others can collect environmental data, and some may collect both types of data. An optical sensor is an example of a sensor that may collect both types of data. Many of the following sensors and data overlap with the biometric sensors and data presented above. They are organized and presented below to indicate the physiological and environmental sources of information.

The blood pressure measurement device or the biometric monitoring device of the present disclosure including a heart rate sensor may use one, some or all of the following sensors to acquire physiological data, including the physiological data outlined in Table 2 below. All combinations and permutations of physiological sensors and/or physiological data are intended to fall within the scope of the present disclosure. The blood pressure measurement device or the biometric monitoring device of the present disclosure may include but is not limited to one, some or all of sensors specified below to acquire the corresponding physiological data; indeed, other type(s) of sensors may be employed to acquire the corresponding physiological data, which are intended to fall within the scope of the present disclosure. Additionally, the device may derive the physiological data from the corresponding sensor output data, but is not limited to the number or types of physiological data that it could derive from said sensor.

TABLE 2

Physiological Sensors and Data

| Physiological Sensors | Physiological data acquired |
| --- | --- |
| Optical Reflectometer | Heart Rate, Heart Rate Variability |
| Potential embodiments: | SpO2 (Saturation of Peripheral Oxygen) |
| Light emitter and receiver | Respiration |
| Multi or single LED and photo diode | Stress |
| arrangement | Blood pressure |
| Wavelength tuned for specific physiological | Arterial Stiffness |
| signals | Blood glucose levels |
| Synchronous detection/amplitude modulation | Blood volume |
| | Heart rate recovery |
| | Cardiac health |
| Motion Detector | Activity level detection |
| Potential embodiments: | Sitting/standing detection |
| Inertial, Gyro or Accelerometer | Fall detection |
| GPS | |
| Skin Temp | Stress |
| EMG | Muscle tension |
| EKG | Heart Rate, Heart Rate Variability, Heart Rate |
| Potential Embodiments: | Recovery |
| 1 lead | Stress |
| 2 lead | Cardiac health |
| Magnetometer | Activity level based on rotation |
| Laser Doppler | Blood flow |
| Power Meter | |
| Ultra Sound | Blood flow |
| Audio | Heart Rate, Heart Rate Variability, Heart Rate |
| | Recovery |
| | Laugh detection |
| | Respiration |
| | Respiration type - snoring, breathing, breathing |
| | problems |
| | User's voice |
| Strain gauge | Heart Rate, Heart Rate Variability |
| Potential embodiment: | Stress |
| In a wrist band | |
| Wet or Humidity sensor | Stress |
| Potential embodiment: | Swimming detection |
| galvanic skin response | Shower detection |

In one exemplary embodiment, the blood pressure measurement device or the biometric monitoring device includes an optical sensor to detect, sense, sample, and/or generate data that may be used to determine information representative of heart rate. In addition, the optical sensor may optionally provide data for determining stress (or level thereof) and/or blood pressure of a user. In one embodiment, the blood pressure measurement device or the biometric monitoring device includes an optical sensor having one or more light sources (LED, laser, etc.) to emit or output light into the user's body and/or light detectors (photodiodes, phototransistors, etc.) to sample, measure and/or detect a response or reflection and provide data used to determine data which is representative of heart rate (e.g., using photoplethysmography (PPG)), stress (or level thereof), and/or blood pressure of a user.

In one exemplary embodiment, a user's heart rate measurement may be triggered by activation criteria determined by one or more sensors (or processing circuitry connected to them). In this embodiment, the one or more sensors function as an activator for the heart rate sensor (i.e., the optical sensor). The criteria are based on information collected by the activator. In some embodiments in which the heart rate sensor gathers on-demand and momentary heart rate data, the activation criteria reflect a single defined user-gesture, such as moving the device in a defined motion trajectory or touching an activator surface area. In contrast, in some embodiments in which the heart rate sensor automatically gathers heart rate data without requiring a defined user gesture, when data from the motion sensor(s) indicates a period of stillness or little motion, the biometric monitoring device may trigger, acquire and/or obtain a heart rate measurement or data. In one embodiment, when the motion sensor(s) indicate user activity or motion (for example, motion that is not suitable or optimum to trigger, acquire and/or obtain desired heart rate measurement or data (for example, data used to determine a user's resting heart rate)), the biometric monitoring device and/or the sensor(s) employed to acquire and/or obtain desired heart rate measurement or data may be placed or remain in a low power state. (Note that measurements taken during motion may be less reliable and may be corrupted by motion artifacts.)

Environmental Sensors

The blood pressure measurement device or the biometric monitoring device of the present disclosure may use one, some or all of the following environmental sensors to, for example, acquire the environmental data, including environmental data outlined in Table 3 below. The blood pressure measurement device or the biometric monitoring device is not limited to the number or types of sensors specified below but may employ other sensors that acquire environmental data outlined in the table below. All combinations and permutations of environmental sensors and/or environmental data are intended to fall within the scope of the present disclosure. Additionally, the device may derive environmental data from the corresponding sensor output data, but is not limited to the types of environmental data that it could derive from said sensor.

The blood pressure measurement device or the biometric monitoring device of the present disclosure may use one or more, or all of the environmental sensors described herein and one or more, or all of the physiological sensors described herein. Indeed, biometric monitoring device of the present disclosure may acquire any or all of the environmental data and physiological data described herein using any sensor now known or later developed—all of which are intended to fall within the scope of the present disclosure.

TABLE 3

Environmental Sensors and Data

| Environmental Sensors | Environmental data acquired |
| --- | --- |
| Motion Detector | Location |
| Potential Embodiments: | Course |
| Inertial, Gyro or Accelerometer | Heading |
| GPS | |
| Pressure/Altimeter sensor | Elevation, elevation |
| Ambient Temp | Temperature |
| Light Sensor | Indoor vs outdoor |
| | Watching TV (spectrum/ flicker rate detection) |
| | Optical data transfer - initiation, QR codes, etc. |
| | ultraviolet light exposure |
| Audio | Indoor vs. Outdoor |
| Compass | Heading |
| Potential Embodiments: | |
| 3 Axis Compass | |

In one embodiment, the blood pressure measurement device or the biometric monitoring device may include an altimeter sensor, for example, disposed or located in the interior of the device housing. In such a case, the device housing may have a vent that allows the interior of the device to measure, detect, sample and/or experience any changes in exterior pressure. In one embodiment, the vent prevents water from entering the device while facilitating measuring, detecting and/or sampling changes in pressure via the altimeter sensor. For example, an exterior surface of the blood pressure measurement device or the biometric monitoring device may include a vent type configuration or architecture (for example, a GORE™ vent) which allows ambient air to move in and out of the housing of the device (which allows the altimeter sensor to measure, detect and/or sample changes in pressure), but reduces, prevents and/or minimizes water and other liquids flow into the housing of the device.

The altimeter sensor, in one embodiment, may be filled with gel that allows the sensor to experience pressure changes outside of the gel. The use of a gel filled altimeter may give the device a higher level of environmental protection with or without the use of an environmentally sealed vent. The device may have a higher survivability rate with a gel filled altimeter in locations including but not limited to those that have high humidity, a clothes washer, a dish washer, a clothes dryer, a steam room, the shower, a pool, and any location where the device may be exposed to moisture, exposed to liquid or submerged in liquid.

It is to be understood that blood pressure measurement devices, in addition to including the features discussed below in more detail, may also include one or more features or functionalities discussed above or discussed in the various applications incorporated by reference in the above discussion. Such implementations are to be understood as being within the scope of this disclosure.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

Importantly, the present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

What is claimed is:

1. A method of obtaining blood pressure data, implemented using an intelligent oscillometric blood pressure measurement (IOBPM) device comprising an inflatable cuff, a pressure sensor, communication circuitry, a memory, and one or more processors, the method comprising:
pairing the IOBPM device and a second device through the communication circuitry, wherein the second device is associated with an identity of a user and the IOBPM is not associated with the identity of the user;
obtaining, by the one or more processors, data associated with the user, wherein the data associated with the user comprise: (a) data indicating that the IOBPM device and the second device are paired, and (b) data indicating the second device is associated with the identity of the user;
obtaining, by the one or more processors, oscillometric blood pressure data from the user and associating the oscillometric blood pressure data with the identity of the user, wherein the oscillometric blood pressure data are generated by the pressure sensor; determining, by the one or more processors, the identity of the user using the oscillometric blood pressure data, comprising applying a classifier to the oscillometric blood pressure data to determine the identity of the user; and
sending, by the one or more processors through the communication circuitry, data indicating the identity of the user and the blood pressure data to the second device.

2. The method of claim 1, further comprising: storing the oscillometric blood pressure data in a user account associated with the identity of the user.

3. The method of claim 1, wherein the pressure sensor is selected from the group consisting of: a force sensor, a force sensitive resistor, a mechanical sensor, a load sensor, a load cell, a strain gauge, a piezo sensor, a membrane potentiometer, and any combination thereof.

4. The method of claim 1, wherein the IOBPM device and the second device are paired through a wireless communication protocol.

5. The method of claim 4, wherein the second device is associated with the user via a hardware characteristic of the second device or via credentials received from an application running on the second device.

6. The method of claim 4, wherein the second device is closest connectable device.

7. The method of claim 1, wherein the data associated with the user comprise biometric data, and wherein determining the identity of the user comprises providing the biometric data to the classifier to determine the identity of the user.

8. The method of claim 7, wherein the biometric data are selected from the group consisting of: motion data, ECG data, PPG data, the oscillometric blood pressure data, arm circumference data, bioelectrical impedance analysis (BIA) data, finger print sensor data, and any combinations thereof.

9. The method of claim 1, wherein the data associated with the user comprise user input specifying the identity of the user.

10. The method of claim 1, wherein the data associated with the user comprise data generated by one or more sensors of the intelligent oscillometric blood pressure measurement device.

11. The method of claim 1, wherein the data associated with the user comprise data that are generated on the second device and obtained through the communication circuitry.

12. The method of claim 1, wherein the intelligent oscillometric blood pressure measurement device comprises a user interface, wherein the method further comprising displaying the identity of the user or information derived therefrom on the user interface of the intelligent oscillometric blood pressure measurement device.

13. The method of claim 1, wherein the second device comprises a user interface, wherein the method further comprises displaying the identity of the user or information derived therefrom on the user interface of the second device.

14. A method of obtaining blood pressure data, implemented using an intelligent oscillometric blood pressure measurement device and a second device, wherein the intelligent oscillometric blood pressure measurement device comprises an inflatable cuff, a pressure sensor, and first communication circuitry, and wherein the second device comprises a memory, second communication circuitry, and one or more processors, the method comprising:
receiving, by the second device, oscillometric blood pressure data from the intelligent oscillometric blood pressure measurement device via the first communication circuitry and the second communication circuitry, wherein the oscillometric blood pressure data are obtained from a user using an oscillometric blood pressure technique, and the oscillometric blood pressure data comprise pressure oscillation data and blood pressure data; and
determining, by the one or more processors of the second device, an identity of the user using the oscillometric blood pressure data, comprising applying a classifier to the oscillometric blood pressure data to determine the identity of the user.

15. The method of claim 14, further comprising causing the blood pressure data to be stored in an account associated with the identity of the user.

16. The method of claim 14, wherein the intelligent oscillometric blood pressure measurement device comprises one or more additional biometric sensors in addition to the pressure sensor, and wherein the user's identity is determined using other biometric data associated with the user that comprise data generated by the one or more additional biometric sensors of the intelligent oscillometric blood pressure measurement device and the other biometric data are obtained through communication between the first communication circuitry and the second communication circuitry.

* * * * *